(12) United States Patent
Lamensdorf et al.

(10) Patent No.: US 8,055,347 B2
(45) Date of Patent: Nov. 8, 2011

(54) STIMULATION FOR TREATING BRAIN EVENTS AND OTHER CONDITIONS

(75) Inventors: Itschak Lamensdorf, Modiin (IL); Avinoam Dayan, Zikron Yaakov (IL); Hernan Altman, Haifa (IL)

(73) Assignee: Brainsgate Ltd., Ra'Anana (IL)

( * ) Notice: Subject to any disclaimer, the term of this patent is extended or adjusted under 35 U.S.C. 154(b) by 1456 days.

(21) Appl. No.: 11/465,381

(22) Filed: Aug. 17, 2006

(65) Prior Publication Data
US 2007/0083245 A1 Apr. 12, 2007

Related U.S. Application Data

(60) Provisional application No. 60/709,734, filed on Aug. 19, 2005.

(51) Int. Cl.
*A61N 1/36* (2006.01)
(52) U.S. Cl. .......................................................... 607/45
(58) Field of Classification Search .................. 607/2, 3, 607/45, 46
See application file for complete search history.

(56) References Cited

U.S. PATENT DOCUMENTS

| | | | |
|---|---|---|---|
| 4,666,829 A | 5/1987 | Glenner et al. |
| 4,866,042 A | 9/1989 | Neuwelt |
| 4,874,694 A | 10/1989 | Gandy et al. |
| 4,907,602 A | 3/1990 | Sanders |
| 4,979,511 A | 12/1990 | Terry, Jr. |
| 5,011,472 A | 4/1991 | Aebischer et al. |
| 5,031,618 A | 7/1991 | Mullett |
| 5,059,415 A | 10/1991 | Neuwelt |
| 5,154,172 A | 10/1992 | Terry, Jr. et al. |

(Continued)

FOREIGN PATENT DOCUMENTS

EP 1559369 8/2005
(Continued)

OTHER PUBLICATIONS

Suzuki, N. et al., "Effect on Cortical Blood Flow of Electrical Stimulation of Trigeminal Cerebrovascular Nerve Fibers in the Rat", Acta Physiol. Scand., 138, 307-315, 1990.
(Continued)

*Primary Examiner* — Niketa Patel
*Assistant Examiner* — Michael D Abreu
(74) *Attorney, Agent, or Firm* — RatnerPrestia

(57) ABSTRACT

Apparatus for treatment is provided, including one or more electrodes, configured to be applied to a site of a subject, and adverse cerebrovascular condition treatment functionality. The functionality comprises a control unit configured to drive the one or more electrodes to apply electrical stimulation to the site during a plurality of stimulation periods which includes at least first and last stimulation periods, set an inter-period interval between initiation of the first stimulation period and initiation of the last stimulation period to be at least 24 hours, and configure the stimulation during the first and last stimulation periods to induce at least one neuroprotective occurrence selected from the group consisting of: an increase in cerebral blood flow (CBF) of the subject, and a release of one or more neuroprotective substances. The site is selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve. Additional embodiments are also described.

32 Claims, 14 Drawing Sheets

U.S. PATENT DOCUMENTS

| | | |
|---|---|---|
| 5,179,950 A | 1/1993 | Stanislaw |
| 5,186,170 A | 2/1993 | Varrichio et al. |
| 5,188,104 A | 2/1993 | Wernicke |
| 5,205,285 A | 4/1993 | Baker, Jr. |
| 5,215,086 A | 6/1993 | Terry, Jr. |
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke |
| 5,268,164 A | 12/1993 | Kozarich et al. |
| 5,269,303 A | 12/1993 | Wernicke et al. |
| 5,299,569 A | 4/1994 | Wernicke |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. |
| 5,351,394 A | 10/1994 | Weinberg |
| 5,531,778 A | 7/1996 | Maschino et al. |
| 5,540,730 A | 7/1996 | Terry, Jr. |
| 5,571,150 A | 11/1996 | Wernicke |
| 5,639,853 A | 6/1997 | Paradiso et al. |
| 5,707,400 A | 1/1998 | Terry, Jr. |
| 5,725,471 A | 3/1998 | Davey et al. |
| 5,752,515 A | 5/1998 | Jolesz et al. |
| 5,756,071 A | 5/1998 | Mattern et al. |
| 5,792,067 A | 8/1998 | Karell |
| 5,792,100 A | 8/1998 | Shantha |
| 5,830,670 A | 11/1998 | De la Monte et al. |
| 5,833,988 A | 11/1998 | Friden |
| 5,849,600 A | 12/1998 | Nixon et al. |
| 5,928,272 A | 7/1999 | Adkins et al. |
| 5,938,689 A | 8/1999 | Fischell et al. |
| 5,938,690 A | 8/1999 | Law et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,061,593 A | 5/2000 | Fischell et al. |
| 6,066,163 A | 5/2000 | John |
| 6,071,705 A | 6/2000 | Wands et al. |
| 6,086,525 A | 7/2000 | Davey et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkow et al. |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,238,892 B1 | 5/2001 | Mercken et al. |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,405,079 B1 | 6/2002 | Ansarinia |
| 6,410,046 B1 | 6/2002 | Lerner |
| 6,415,184 B1 | 7/2002 | Ishikawa et al. |
| 6,459,936 B2 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Fischell et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,647,296 B2 | 11/2003 | Fischell et al. |
| 6,662,035 B2 | 12/2003 | Sochor |
| 6,678,553 B2 | 1/2004 | Lerner et al. |
| 6,690,974 B2 | 2/2004 | Archer et al. |
| 6,735,474 B1 | 5/2004 | Loeb et al. |
| 6,810,285 B2 | 10/2004 | Pless et al. |
| 6,811,788 B2 | 11/2004 | Yu |
| 6,853,858 B2 | 2/2005 | Shalev |
| 6,905,827 B2 | 6/2005 | Wohlgemuth et al. |
| 6,922,590 B1 | 7/2005 | Whitehurst |
| 7,117,033 B2 | 10/2006 | Shalev et al. |
| 7,120,489 B2 | 10/2006 | Shalev et al. |
| 2001/0004644 A1 | 6/2001 | Levin |
| 2001/0014670 A1 | 8/2001 | Balin et al. |
| 2001/0018191 A1 | 8/2001 | Mercken et al. |
| 2001/0020097 A1 | 9/2001 | Audia et al. |
| 2001/0026916 A1 | 10/2001 | Ginsberg et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0040032 A1 | 4/2002 | Glasky et al. |
| 2002/0040052 A1 | 4/2002 | Ito et al. |
| 2002/0042121 A1 | 4/2002 | Riesner et al. |
| 2002/0042420 A1 | 4/2002 | Briem et al. |
| 2002/0044919 A1 | 4/2002 | Yu |
| 2002/0052311 A1 | 5/2002 | Solomon et al. |
| 2002/0055501 A1 | 5/2002 | Olson et al. |
| 2002/0066959 A1 | 6/2002 | Joshi |
| 2002/0068080 A1 | 6/2002 | Lerner |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |

| | | | |
|---|---|---|---|
| 2003/0050527 A1 | 3/2003 | Fox et al. | |
| 2003/0051268 A1 | 3/2003 | Allen | |
| 2003/0056238 A1 | 3/2003 | Wisotzkey | |
| 2003/0073917 A1 | 4/2003 | Echauz et al. | |
| 2003/0074033 A1 | 4/2003 | Pless et al. | |
| 2003/0079742 A1 | 5/2003 | Giroux | |
| 2003/0106083 A1 | 6/2003 | Allen | |
| 2003/0131367 A1 | 7/2003 | Guenther et al. | |
| 2003/0133877 A1 | 7/2003 | Levin | |
| 2003/0144711 A1 | 7/2003 | Pless et al. | |
| 2003/0149457 A1 | 8/2003 | Tcheng et al. | |
| 2003/0166099 A1 | 9/2003 | Sabbadini et al. | |
| 2003/0166279 A1 | 9/2003 | Sabbadini et al. | |
| 2003/0172390 A1 | 9/2003 | Wisotzkey et al. | |
| 2003/0176892 A1 | 9/2003 | Shalev | |
| 2003/0176898 A1 | 9/2003 | Gross et al. | |
| 2003/0177514 A1 | 9/2003 | Leviten | |
| 2003/0190601 A1 | 10/2003 | Sabbadini et al. | |
| 2003/0190683 A1 | 10/2003 | Sabbadini et al. | |
| 2003/0190749 A1 | 10/2003 | Surber et al. | |
| 2003/0191426 A1 | 10/2003 | Lerner et al. | |
| 2003/0194714 A1 | 10/2003 | Sabbadini et al. | |
| 2003/0195588 A1 | 10/2003 | Fischell et al. | |
| 2003/0195602 A1 | 10/2003 | Boling | |
| 2003/0198995 A1 | 10/2003 | Sabbadini et al. | |
| 2003/0198996 A1 | 10/2003 | Surber et al. | |
| 2003/0199005 A1 | 10/2003 | Sabbadini et al. | |
| 2003/0199088 A1 | 10/2003 | Sabbadini et al. | |
| 2003/0199089 A1 | 10/2003 | Surber et al. | |
| 2003/0202937 A1 | 10/2003 | Sabbadini et al. | |
| 2003/0203411 A1 | 10/2003 | Sabbadini et al. | |
| 2003/0203481 A1 | 10/2003 | Surber et al. | |
| 2003/0207833 A1 | 11/2003 | Berkley et al. | |
| 2003/0211086 A1 | 11/2003 | Berkley et al. | |
| 2003/0211599 A1 | 11/2003 | Sabbadini et al. | |
| 2003/0219408 A1 | 11/2003 | Sabbadini et al. | |
| 2003/0219888 A1 | 11/2003 | Segall et al. | |
| 2003/0224369 A1 | 12/2003 | Surber et al. | |
| 2003/0224444 A1 | 12/2003 | Sabbadini et al. | |
| 2003/0232335 A1 | 12/2003 | Surber et al. | |
| 2004/0015068 A1* | 1/2004 | Shalev et al. | 600/378 |
| 2004/0033491 A1 | 2/2004 | Alsobrook et al. | |
| 2004/0054297 A1 | 3/2004 | Wingeier et al. | |
| 2004/0133248 A1 | 7/2004 | Frei et al. | |
| 2004/0136950 A1 | 7/2004 | Ni et al. | |
| 2004/0136951 A1 | 7/2004 | Ni et al. | |
| 2004/0153129 A1 | 8/2004 | Pless et al. | |
| 2004/0210269 A1 | 10/2004 | Shalev et al. | |
| 2004/0220644 A1 | 11/2004 | Shalev et al. | |
| 2005/0020519 A1 | 1/2005 | Albiston et al. | |
| 2005/0054939 A1 | 3/2005 | Ben-Ari et al. | |
| 2005/0074506 A1 | 4/2005 | Natan et al. | |
| 2005/0112090 A9 | 5/2005 | Ni | |
| 2005/0118187 A1 | 6/2005 | Yu | |
| 2005/0137646 A1 | 6/2005 | Wallace et al. | |
| 2005/0137647 A1 | 6/2005 | Wallace et al. | |
| 2005/0159790 A1 | 7/2005 | Shalev | |
| 2006/0287677 A1 | 12/2006 | Shalev et al. | |

FOREIGN PATENT DOCUMENTS

| | | |
|---|---|---|
| WO | WO-97/18855 | 5/1997 |
| WO | WO-99/03473 | 1/1999 |
| WO | WO-00/44432 | 8/2000 |
| WO | WO-00/73343 | 12/2000 |
| WO | WO-01/00402 A1 | 1/2001 |
| WO | WO-01/43733 | 6/2001 |
| WO | WO-01/85094 A2 | 11/2001 |
| WO | WO-01/97905 A1 | 12/2001 |
| WO | WO-02/32504 | 4/2002 |
| WO | WO-02/068029 | 9/2002 |
| WO | WO-02/068031 | 9/2002 |
| WO | WO-02/094191 | 11/2002 |
| WO | WO-03/000310 | 1/2003 |
| WO | WO-03/020350 | 3/2003 |
| WO | WO-03/063959 | 8/2003 |
| WO | WO-03/084591 | 10/2003 |
| WO | WO-03/090599 | 11/2003 |
| WO | WO-03/105658 | 12/2003 |
| WO | WO-2004/010923 | 2/2004 |
| WO | WO-2004/043217 | 5/2004 |
| WO | WO-2004/043218 | 5/2004 |
| WO | WO-2004/043334 | 5/2004 |
| WO | WO-2004/044947 | 5/2004 |
| WO | WO-2004/045242 | 5/2004 |
| WO | WO-2004/064918 A1 | 8/2004 |
| WO | WO-2005/030025 | 4/2005 |
| WO | WO-2005/030118 | 4/2005 |
| WO | WO-2006/021957 | 3/2006 |

OTHER PUBLICATIONS

Fusco BM, Fiore G, Gallo F, Martelletti P, Giacovazzo M, "Capsaicin-sensitive' sensory neurons in cluster headache: pathophysiological aspects and therapeutic indications," Headache, 34, 132-137 (1994).

Silver WL, "Neural and pharmacological basis for nasal irritation," in Tucker WG, Leaderer BP, Molhave L, Cain WS (eds), Sources of Indoor Air Contaminants, Ann. NY Acad. Sci., 641, 152-163 (1992).

Lambert GA, Bogduk N, Goadsby PJ, Duckworth JW, Lance JW, "Decreased carotid arterial resistance in cats in response to trigeminal stimulation," Journal of Neurosurgery, 61, 307-315 (1984).

Branimir I. Sikic, et al., "Modulation and preventiion of multidrug resistance by inhibitors of P-glycoprotein", Cancer Chemother Pharmacol (1997), 40 (Suppl):S13-S19.

Fu Yung-Hui, et al., "Improved bioavailability of orally administered drugs by Chinese herbal enhancers through modulation of P-glycoprotein", ASHP 39th Midyear Clinical Meeting and Exhibits, Dec. 5-9, 2004.

Delephine, et al., "Plasma Protein Extravasation Induced in the Rat Dura Mater by Stimulation of the Parasympathetic Sphenopalatine Ganglion" Experimental Neurology, 147, 389-400, 1997.

Hara H. Zhang, et al., "Parasympathetic Cerebrovascular Innervation: An Anterograde Tracing from the Sphenopalatine Ganglion in the Rat", Neurosurgery, 32 822-827, 1993.

G.L. Ruskell,"The Orbital Branches of the Pterygopalatine Ganglion and their Relationship with Internal Carotid Nerve Branches in Primates'" J. Anat. 1970,106,2, pp. 323-339.

Kroll RA, Neuwelt EA, "Outwitting the Blood Brain Barrier for Therapeutic Purposes: Osmotic Opening and Other Means", Neurosurgery, 42, 1083-1100, 1998.

Sanders M, et al., "Efficacy of Sphenopalatine Ganglion Blockade in 66 Patients Suffering from Cluster Headache: A 12-70 Month Follow-Up Evaluation", Journal of Neurosurgery, 87 876-880, 1997.

Suzuki, N. et al. "Selective Electrical Stimulation of postganglionic Cerebrovascular Parasympathetic Nerve Fibers Originating from the Sphenopalatine Ganglion Enhances Cortical Blood Flow in the Rat'" Journal of Cerebral Blood Flow and Metabolism, 10 383-391 (1990).

Samad TA et al., in an article entitled, "Interleukin-1beta-mediatyed induction of Cox-2 in the CNS contributes to inflammatory pain hypersensitivity, " in Nature 410(6827): 471-5 (2001).

Van de WaterBeemd, et al., "Estimation of Blood Brain Barrier Crossing of Drugs Using Molecular Sze and Shape and H bonding Descriptors" Journal of Drug Targeting, 6, 151-165, 1998.

Ronald F. Young, "Electrical Stimulation of the Trigeminal nerve root for the Treatment of Chronic Facial Pain", J Neurosurg 83:72-78, 1995.

N. Suzuki, et al., "Origins and Pathways of Cerebrovascular Vasoactive Intestinal Polypeptide-Positive Nerves in Rat'" J Cereb Blood Flow Metab. vol. 8 No. 5, 1988.

J.M. Gallo, et al., "The effect of P-glycoprotein on Paclitaxel Brain and Brain Tumor Distribution in Mice" Cancer Research 63, 5114-5117, Aug. 2003.

Supplementary European Search Report dated Oct. 27, 2009 which issued during the prosecution of applicant's European Patent Application No. 04 77 0568.

Reis et al., "Electrical Stimulation of Cerebellar Fastigial Nucleus Reduces Ischemic Infarction Elicited by Middle Cerebral Artery Occlusion in Rat," Journal of Cerebral Blood Flow and Metabolism, 11:810-818, 1991.

Nollet et al., "Transcranial magnetic stimulation: review of the technique, basic principles and applications," The Veterinary Journal, 166 (2003) 28-42.

Devoghel JC, "Cluster headache and spenopalatine block," Acta Anaesthesiol Belg., 1981, 32, 101-107, an abstract.

Office Action dated Jul. 16, 2008, which issued during the prosecution of Applicants' U.S. Appl. No. 11/349,020.

Office Action dated Jun. 27, 2008, which issued during the prosecution of Applicants' U.S. Appl. No. 10/518,322.

* cited by examiner

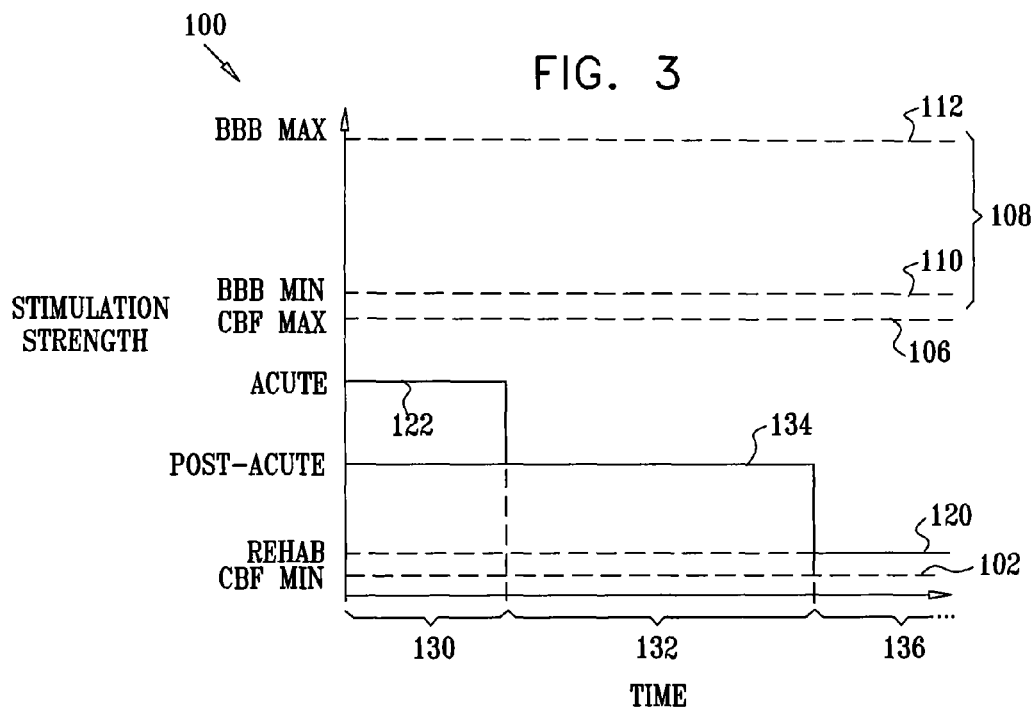
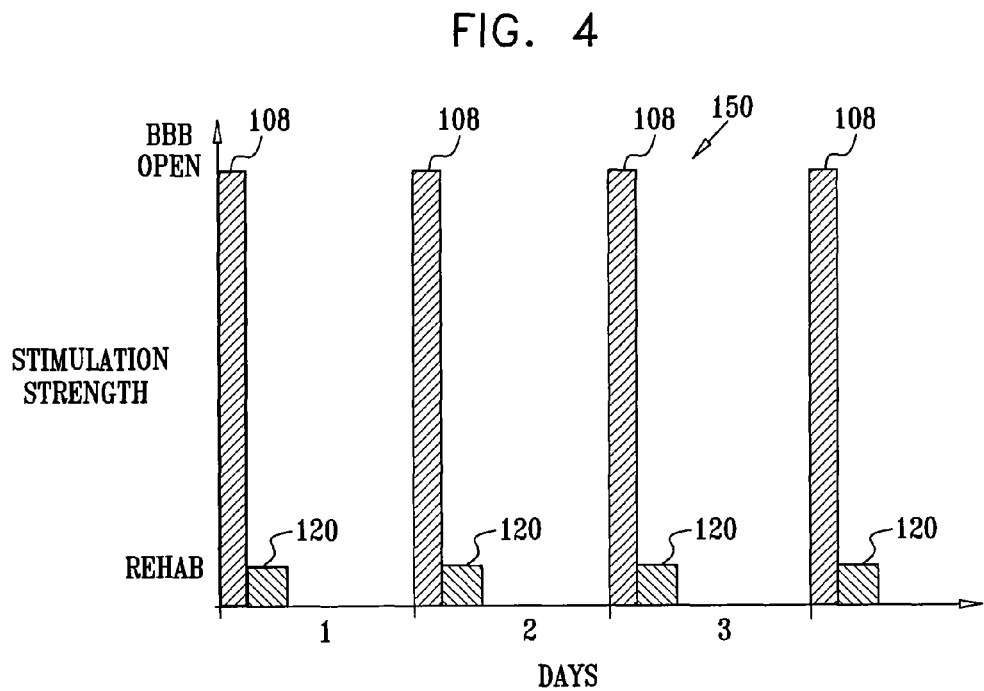

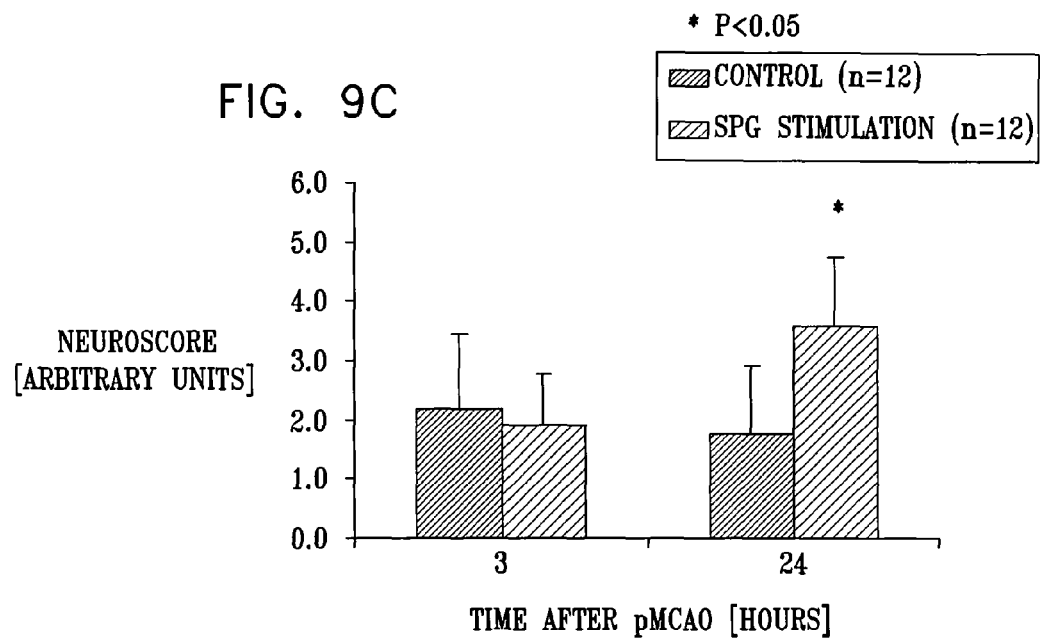
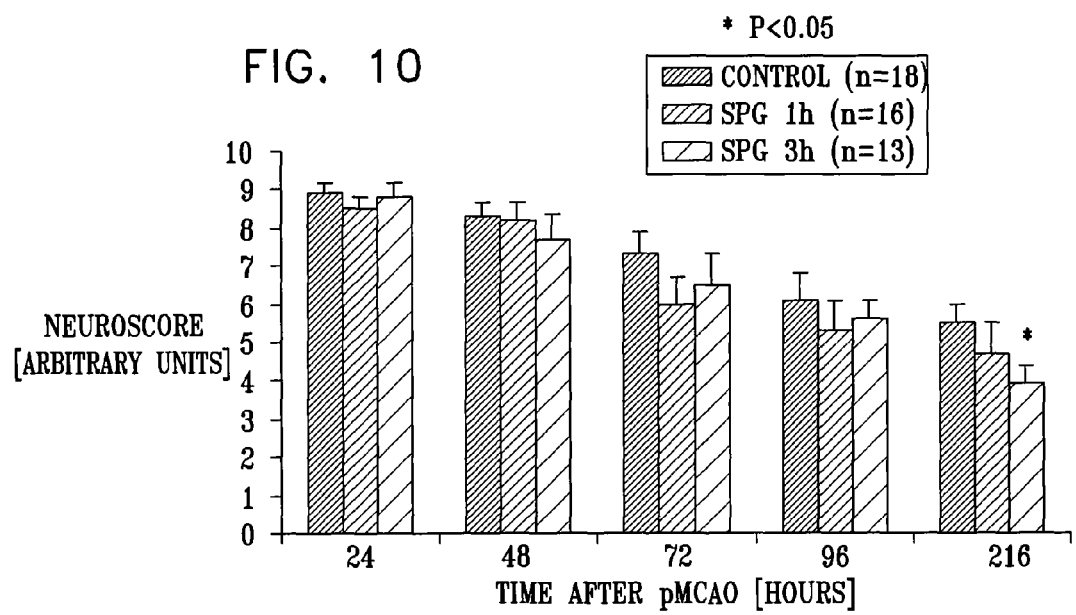

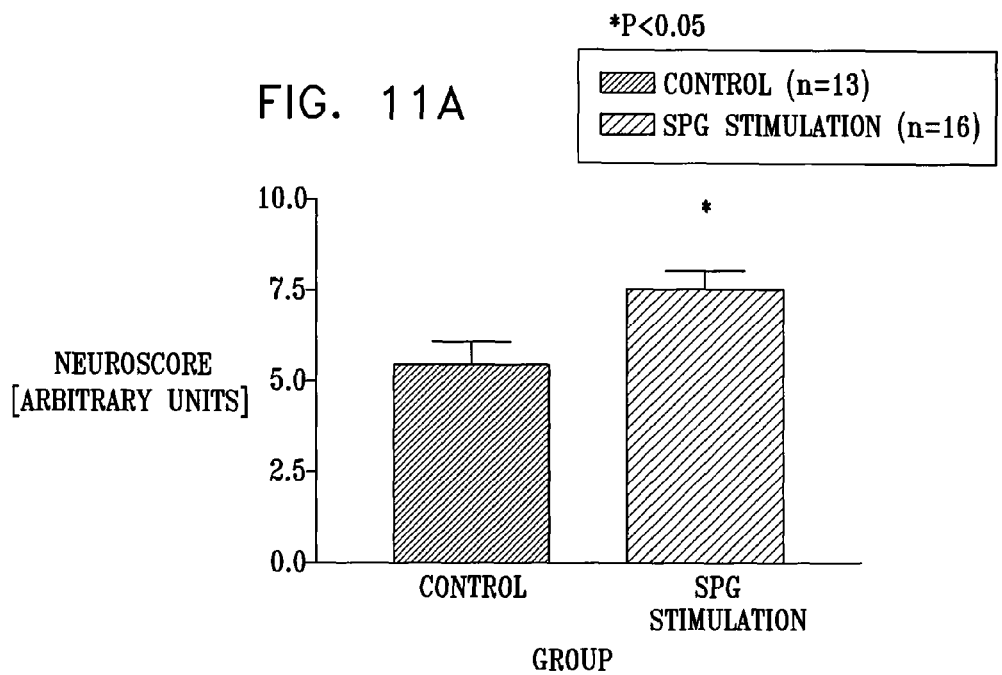
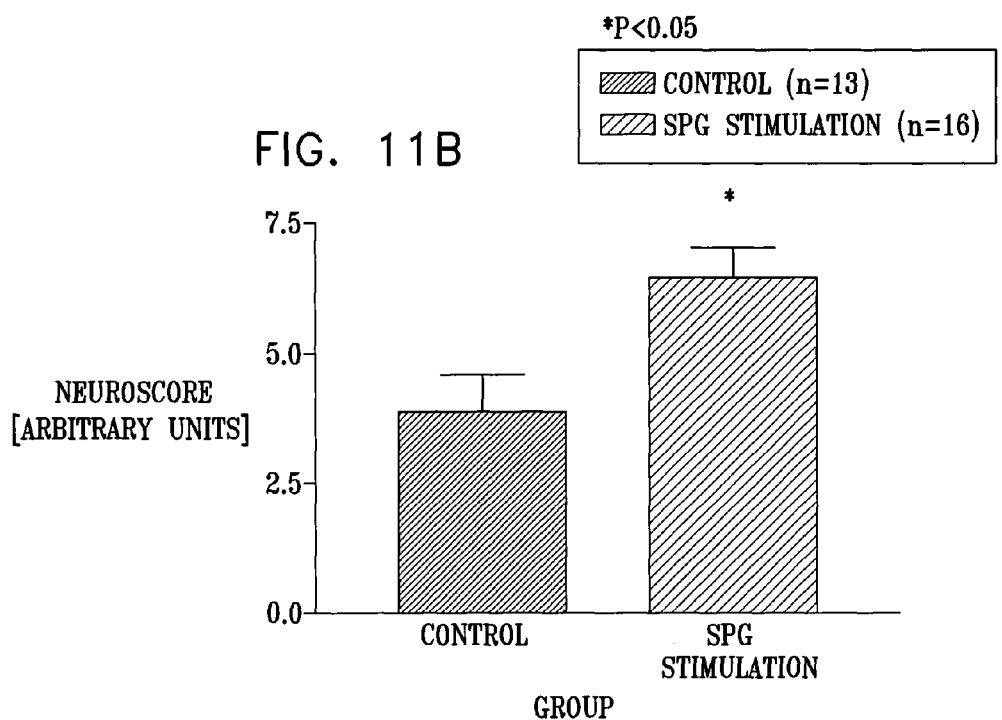

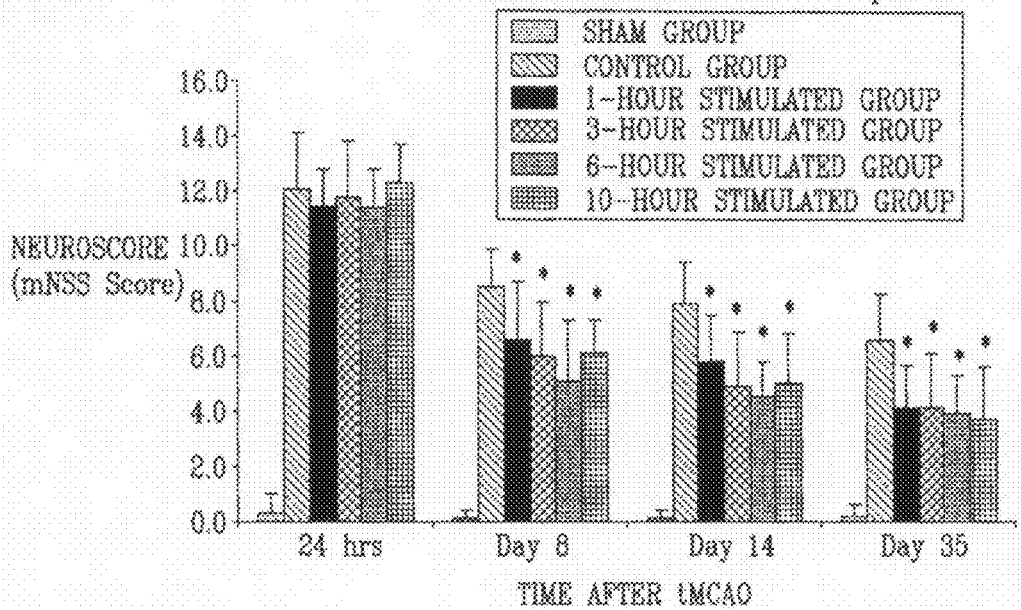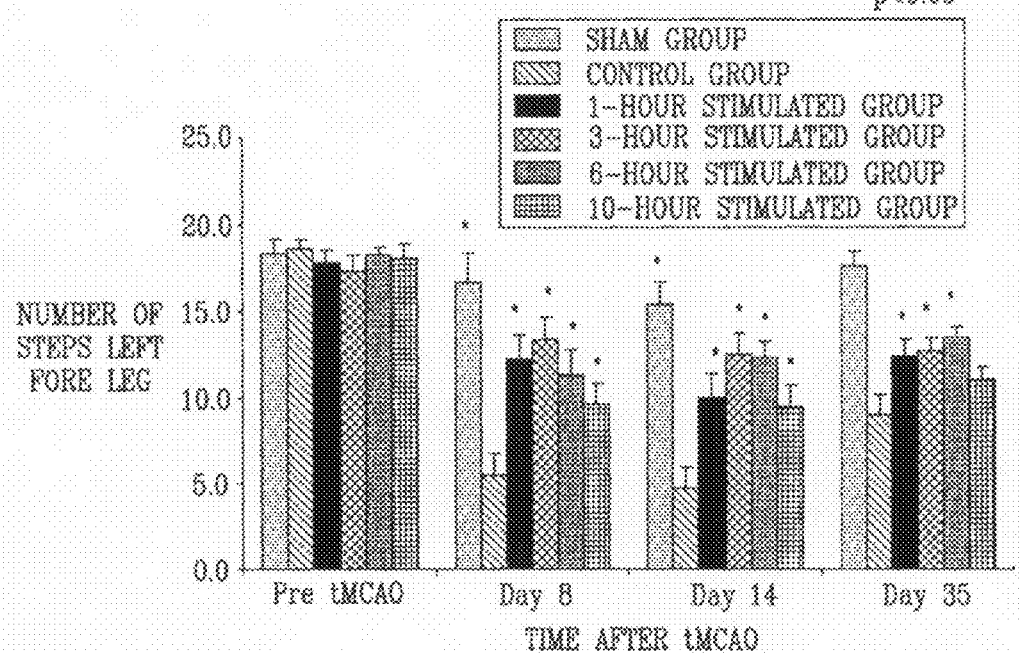

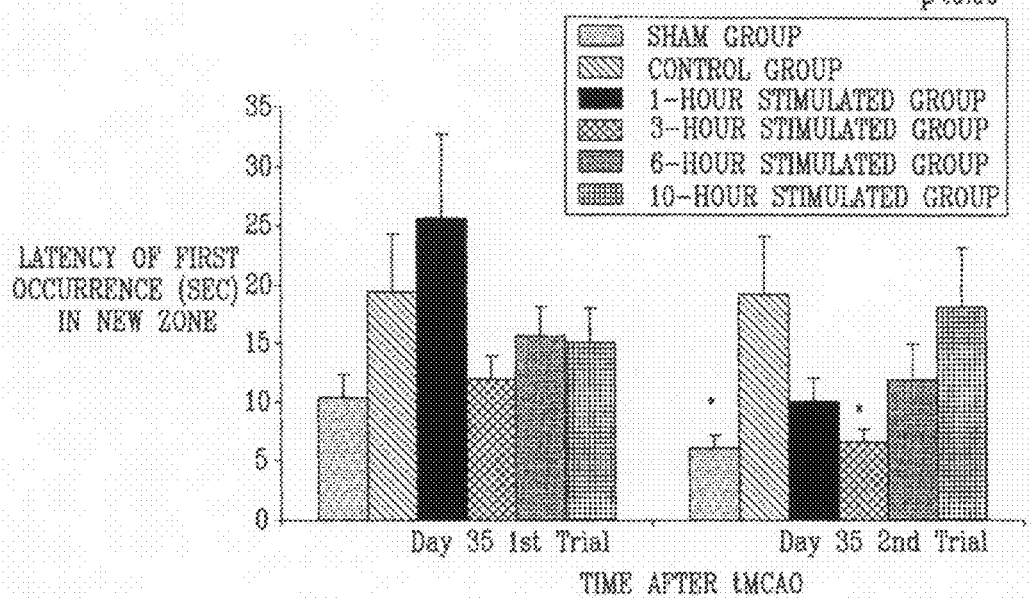
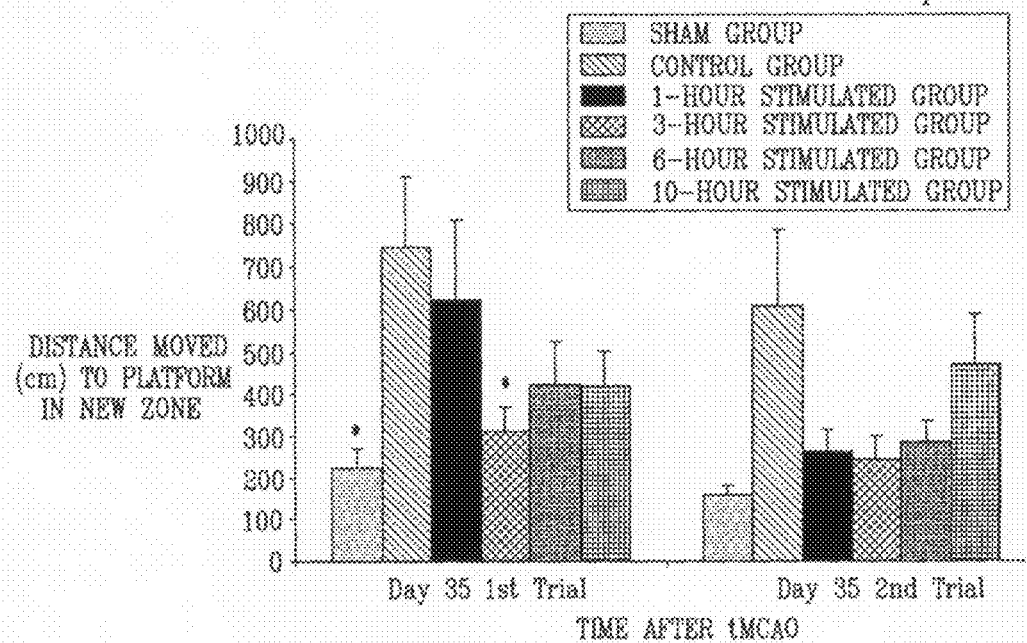

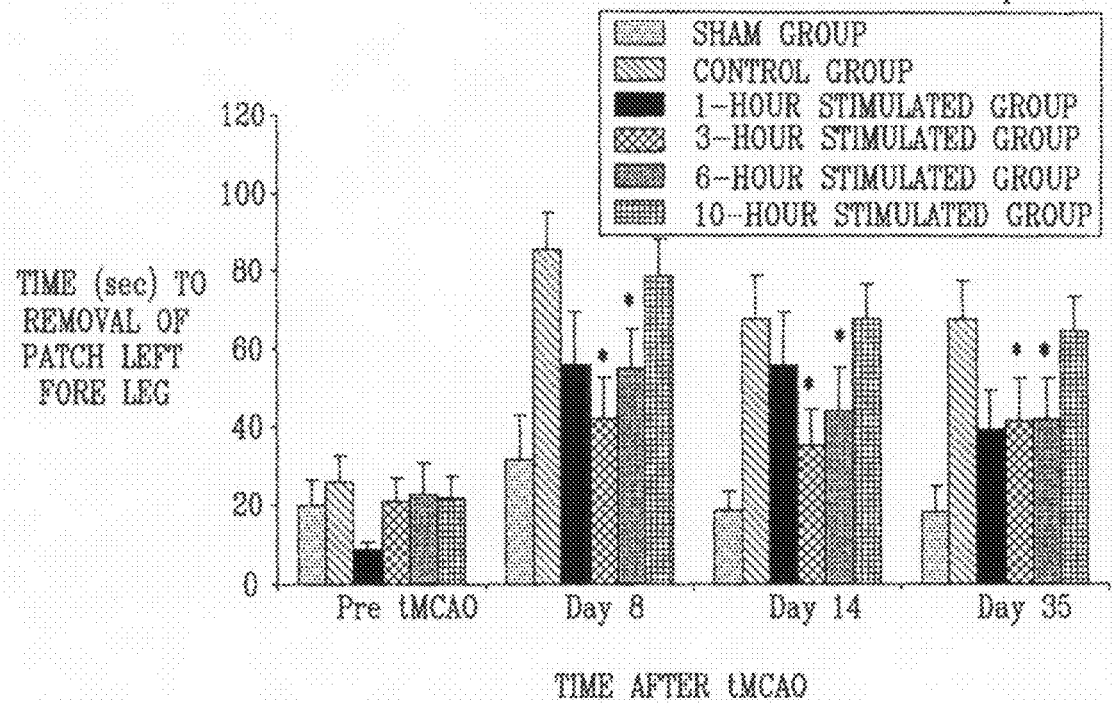
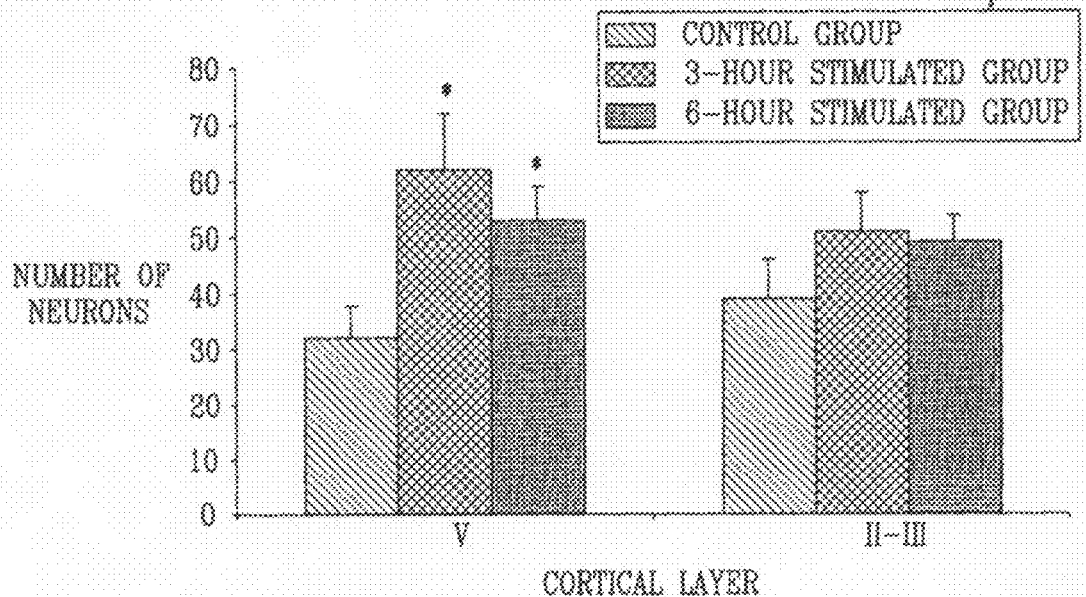

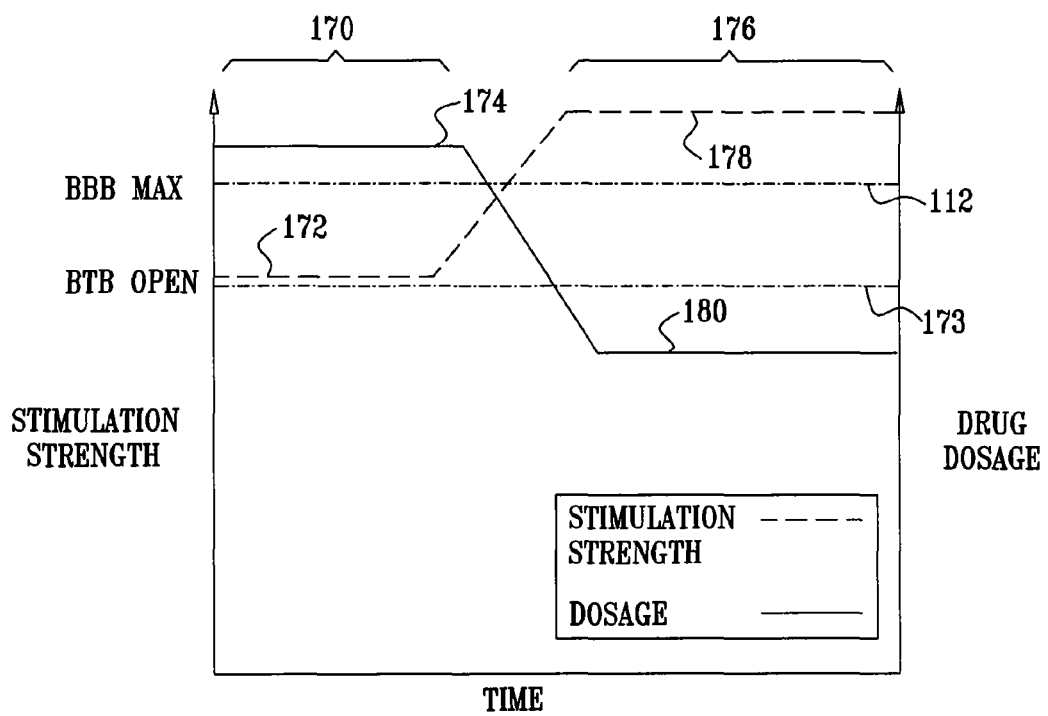

STIMULATION FOR TREATING BRAIN EVENTS AND OTHER CONDITIONS

CROSS-REFERENCES TO RELATED APPLICATIONS

The present application claims the benefit of U.S. Provisional Application 60/709,734, filed Aug. 19, 2005, entitled, "Stimulation for treating brain events and other conditions," which is assigned to the assignee of the present application and is incorporated herein by reference, including the appendices thereof.

The present application is related to a European patent application filed on even date herewith, entitled, "Stimulation for treating brain events and other conditions."

FIELD OF THE INVENTION

The present invention relates generally to medical procedures and devices. More specifically, the invention relates to the use of stimulation for treating medical conditions.

BACKGROUND OF THE INVENTION

The blood-brain barrier (BBB) is a unique feature of the central nervous system (CNS) which isolates the brain from the systemic blood circulation. To maintain the homeostasis of the CNS, the BBB prevents access to the brain of many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the BBB by the synthesis and secretion of soluble growth factors (e.g., gamma-glutamyl transpeptidase) essential for the endothelial cells to develop their BBB characteristics.

PCT Publication WO 01/85094 and US Patent Application Publications 2004/0015068 and 2004/0210269 to Shalev and Gross, which are assigned to the assignee of the present patent application and are incorporated herein by reference, describe apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 6,853,858 to Shalev, which is assigned to the assignee of the present application and is incorporated herein by reference, describes apparatus for delivering a Non Steroidal Anti-Inflammatory Drug (NSAID) supplied to a body of a subject for delivery to at least a portion of a central nervous system (CNS) of the subject via a systemic blood circulation of the subject. The apparatus includes a stimulator adapted to stimulate at least one site of the subject, so as to cause an increase in passage of the NSAID from the systemic blood circulation across a blood brain barrier (BBB) of the subject to the portion of the CNS, during at least a portion of the time that the NSAID is present in the blood, the site selected from the group consisting of: a sphenopalatine ganglion (SPG), an anterior ethmoidal nerve, a posterior ethmoidal nerve, a communicating branch between an anterior ethmoidal nerve and a retro-orbital branch of an SPG, a communicating branch between a posterior ethmoidal nerve and a retro-orbital branch of an SPG, a greater palatine nerve, a lesser palatine nerve, a sphenopalatine nerve, a communicating branch between a maxillary nerve and an SPG, a nasopalatine nerve, a posterior nasal nerve, an infraorbital nerve, an otic ganglion, an afferent fiber going into the otic ganglion, an efferent fiber going out of the otic ganglion, a vidian nerve, a greater superficial petrosal nerve, and a lesser deep petrosal nerve.

US Patent Application Publication 2004/0220644 to Shalev et al., which is assigned to the assignee of the present application and is incorporated herein by reference, describes a method for treating a subject, including positioning at least one electrode at at least one site of the subject, such as the SPG, for less than about 3 hours, applying an electrical current to the site of the subject, and configuring the current to increase cerebral blood flow (CBF) of the subject, so as to treat a condition of the subject.

US Patent Application Publication 2003/0176898 to Gross et al., which is assigned to the assignee of the present application and is incorporated herein by reference, describes apparatus for treating a condition of an eye of a subject, comprising a stimulator adapted to stimulate at least one site of the subject, such as the SPG, so as to treat the eye condition.

US Patent Application Publication 2005/0159790 to Shalev, which is assigned to the assignee of the present application and is incorporated herein by reference, describes a method for facilitating a diagnosis of a condition of a subject, including applying a current to a site of the subject, such as the SPG, and configuring the current to increase conductance of molecules from brain tissue of the subject through a blood brain barrier (BBB) of the subject into a systemic blood circulation of the subject. The method also includes sensing a quantity of the molecules from a site outside of the brain of the subject, following initiation of application of the current.

US Patent Application Publication 2005/0266099 to Shalev, which is assigned to the assignee of the present application and is incorporated herein by reference, describes a method for modifying a property of a brain of a patient includes presenting an odorant to an air passage of the patient, the odorant having been selected for presentation to the air passage because it is such as to increase conductance of molecules from a systemic blood circulation of the patient through a blood brain barrier (BBB) of the brain into brain tissue of the patient. The molecules are selected from the group consisting of: a pharmacological agent, a therapeutic agent, an endogenous agent, and an agent for facilitating a diagnostic procedure.

PCT Publication WO 04/010923 to Gross et al., which is assigned to the assignee of the present application and is incorporated herein by reference, describes a chemical agent delivery system, including a chemical agent supplied to a body of a subject for delivery to a site in a central nervous system of said subject via blood of said subject; and a stimulator for stimulating parasympathetic fibers associated with the SPG, thereby rendering a blood brain barrier (BBB) of said subject permeable to said chemical agent during at least a portion of the time that said chemical agent is present in said blood.

PCT Publication WO 04/043218 to Gross et al., which is assigned to the assignee of the present application and is incorporated herein by reference, describes apparatus for treating a subject, including (a) a stimulation device, adapted to be implanted in a vicinity of a site selected from the list consisting of: a SPG and a neural tract originating in or leading to the SPG; and (b) a connecting element, coupled to the stimulation device, and adapted to be passed through at least a portion of a greater palatine canal of the subject.

PCT Publication WO 04/045242 to Shalev, which is assigned to the assignee of the present application and is incorporated herein by reference, describes apparatus for treating a condition of an ear of a subject, comprising a stimulator adapted to stimulate at least one site of the subject, such as the SPG, at a level sufficient to treat the ear condition.

PCT Publication WO 05/030025 to Shalev et al., which is assigned to the assignee of the present application and is incorporated herein by reference, describes apparatus for treating a subject, including an elongated generally rigid support element having a length of at least 1.8 cm, and having a distal end. The apparatus also includes one or more electrodes fixed to the support element in a vicinity of the distal end thereof, and configured to be positioned in a vicinity of a site of the subject, such as the SPG, when the support element is inserted into a body of the subject, such that a portion of the support element remains outside of the body. The apparatus further includes a control unit, coupled to the support element, and adapted to drive the electrodes to apply an electrical current to the site, and to configure the current to increase cerebral blood flow (CBF) of the subject, so as to treat a condition of the subject.

U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site.

U.S. Pat. No. 6,432,986 to Levin and PCT Publication WO 99/03473 to Levin, which are incorporated herein by reference, describe techniques for inhibiting a cerebral neurovascular disorder or a muscular headache. The techniques include intranasally administering a pharmaceutical composition comprising a long-acting local anesthetic.

U.S. Pat. No. 6,491,940 to Levin, US Patent Application 2003/0133877 to Levin, and PCT Publication WO 00/44432 to Levin, which are incorporated herein by reference, describe techniques for inhibiting a cerebral neurovascular disorder or a muscular headache. The techniques include intranasally administering a pharmaceutical composition comprising a long-acting local anesthetic. Apparatus for delivering or applying the composition is also described.

US Patent Application 2001/0004644 to Levin and PCT Publication WO 01/43733 to Levin, which are incorporated herein by reference, describe techniques for inhibiting cephalic inflammation, including meningeal inflammation and cerebral inflammation. The techniques include intranasally administering a long-acting local anesthetic. Apparatus for delivering or applying the composition is also described, including a dorsonasally implanted electronic neural stimulator, such as a transepithelial neural stimulation device.

The following patent application publications, all of which are assigned to the assignee of the present application and are incorporated herein by reference, may be of interest: WO 03/090599, WO 03/105658, WO 04/010923, WO 04/043218, WO 04/044947, WO 04/045242, WO 04/043217, WO 04/043334, WO 05/030025, WO 05/030118, and US 2004/0220644.

The following patents and patent application publications, all of which are incorporated herein by reference, may be of interest: U.S. Pat. No. 5,756,071 to Mattern et al., U.S. Pat. No. 5,752,515 to Jolesz et al., U.S. Pat. Nos. 5,725,471 and 6,086,525 to Davey et al., PCT Publication WO 02/32504 to Zanger et al., US Patent Application Publication 2003/0050527 to Fox et al., U.S. Pat. No. 6,415,184 to Ishikawa et al., PCT Publications WO 03/084591, WO 03/020350, WO 03/000310, WO 02/068031, and WO 02/068029 to Djupesland, and US Patent Application Publication 2003/0079742 to Giroux.

Hotta H et al., in an article entitled, "Effects of stimulating the nucleus basalis of Meynert on blood flow and delayed neuronal death following transient ischemia in rat cerebral cortes," Jap J Phys 52:383-393 (2002), which is incorporated herein by reference, report that stimulation of the nucleus basalis of Meynert (NBM) in the rat was accompanied by vasodilatation and increase in cortical blood flow. They suggest that NBM-originating vasodilative activation can protect the ischemia-induced delayed death of cortical neurons by preventing a blood flow decrease in widespread cortices.

Reis D J et al., in an article entitled, "Electrical stimulation of cerebellar fastigial nucleus reduces ischemic infarction elicited by middle cerebral artery occlusion in rat," J Cereb Blood Flow Metab 11(5):810-8 (1991), which is incorporated herein by reference, report that electrical stimulation of the cerebellar fastigial nucleus (FN) profoundly increases cerebral blood flow via a cholinergic mechanism. Utilizing the rat middle cerebral artery occlusion (MCAO) model, they demonstrated that one hour of electrical stimulation of the FN has the capacity to substantially reduce the infarct size at the rim of the cortex dorsal and ventral to the infarction, and medially within the thalamus and striatum corresponding to the penumbral zone. They conclude that excitation of an intrinsic system in brain represented in the rostral FN has the capacity to substantially reduce an ischemic infarction.

Matsui T et al., in an article entitled, "The effects of cervical spinal cord stimulation (cSCS) on experimental stroke," Pacing Clin Electrophysiol 12(4 Pt 2):726-32 (1989), which is incorporated herein by reference, report that cSCS increases regional cerebral blood flow, and, in a cat middle cerebral artery occlusion model (MCAO), reduced the rate of death within 24 hours after MCAO.

Segher O et al., in an article entitled, "Spinal cord stimulation reducing infract volume in model of focal cerebral ischemia in rats," J Neurosurg 99(1):131-137 (2003), which is incorporated herein by reference, demonstrate that spinal cord stimulation increases cerebral blood flow in rats and significantly reduces stroke volume, suggesting that spinal cord stimulation could be used for treatment and prevention of stroke.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389-400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822-827 (1993)

Jolliet-Riant P, Tillement J P, "Drug transfer across the blood-brain barrier and improvement of brain delivery," Fundam. Clin. Pharmacol., 13, 16-25 (1999)

Kroll R A, Neuwelt E A, "Outwitting the blood brain barrier for therapeutic purposes: Osmotic opening and other means," Neurosurgery, 42, 1083-1100 (1998)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875-878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151-165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307-315 (1990)

Major A, Silver W, "Odorants presented to the rat nasal cavity increase cortical blood flow," Chem. Senses, 24, 665-669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132-137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307-315 (1984)

Silver W L, "Neural and pharmacological basis for nasal irritation," in Tucker W G, Leaderer B P, Molhave L, Cain W S (eds), Sources of Indoor Air Contaminants, Ann. NY Acad. Sci., 641, 152-163 (1992)

Silver W, "Chemesthesis: the burning questions," ChemoSense, Vol. 2, 1-2 (1999)

Devoghel J C, "Cluster headache and sphenopalatine block," Acta Anaesthesiol Belg., 32(1):101-7 (1981)

Branston N M, "The physiology of the cerebrovascular parasympathetic innervation," British Journal of Neurosurgery 9:319-329 (1995)

Branston N M et al., "Contribution of cerebrovascular parasympathetic and sensory innervation to the short-term control of blood flow in rat cerebral cortex," J Cereb Blood Flow Metab 15(3):525-31 (1995)

Toda N et al., "Cerebral vasodilation induced by stimulation of the pterygopalatine ganglion and greater petrosal nerve in anesthetized monkeys," Neuroscience 96(2):393-398 (2000)

Seylaz J et al., "Effect of stimulation of the sphenopalatine ganglion on cortical blood flow in the rat," J Cereb Blood Flow Metab 8(6):875-8 (1988)

Nollet H et al., "Transcranial magnetic stimulation: review of the technique, basic principles and applications," The Veterinary Journal 166:28-42 (2003)

Van Gijn J et al., "Subarachnoid haemorrhage: diagnosis, causes and management," Brain 124:249-278 (2001)

Goadsby P J et al., "Effect of stimulation of trigeminal ganglion on regional cerebral blood flow in cats," Am J Physiol 22:R270-R274 (1987)

Walters B B et al., "Cerebrovascular projections from the sphenopalatine and otic ganglia to the middle cerebral artery of the cat," Stroke 17:488-494 (1986)

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989)

Roth B J et al., "In vitro evaluation of a 4-leaf coil design for magnetic stimulation of peripheral nerve," Electroencephalography and Clinical Neurophysiology 93:68-74 (1994)

Zhang R et al., "A nitric oxide donor induces neurogenesis and reduces functional deficits after stroke in rats," Ann Neurol 50:602-611 (2001)

Ziche M et al., "Nitric oxide and angiogenesis," J Neurooncol 50:139-148 (2000)

Kawamata T et al., "Intracisternal basic fibroblast growth factor (bFGF) enhances behavioral recovery following focal cerebral infarction in the rat," J Cereb Blood Flow Metab 16:542-547 (1996)

Zhang Z G et el., "VEGF enhances angiogenesis and promotes blood-brain barrier leakage in the ischemic brain," J Clin Invest 106:829-838 (2000)

Sun Y et al., "Neuronal nitric oxide synthase and ischemia-induced neurogenesis," J Cereb Blood Flow Metab 25(4): 485-92 (2005)

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994)

Beridze M et al., "Effect of nitric oxide initial blood levels on erythrocyte aggregability during 12 hours from ischemic stroke onset," Clin Hemorheol Microcirc 30(3-4):403-6 (2004)

Davis S M et al., "Advances in penumbra imaging with MR," Cerebrovasc Dis 17 Suppl 3:23-7 (2004)

Phan T G et al., "Salvaging the ischaemic penumbra: more than just reperfusion?" Clin Exp Pharmacol Physiol 29(1-2):1-10 (2002)

Gressens P et al., "Neuroprotection of the developing brain by systemic administration of vasoactive intestinal peptide derivatives," J Pharmacol Exp Ther 288 (3):1207-13 (1999)

Zhang R et al., "Nitric oxide enhances angiogenesis via the synthesis of vascular endothelial growth factor and cGMP after stroke in the rat," Circ Res 21; 92(3):308-13 (2003)

de la Torre J C, "Vascular basis of Alzheimer's pathogenesis," Ann NY Acad Sci 977:196-215 (2002)

Roman G C, "Cholinergic dysfunction in vascular dementia," Curr Psychiatry Rep 7(1):18-26 (2005)

Tony J F L, "Nitric oxide and the cerebral vascular function," J Biomed Sci 7:16-26 (2000)

Pluta R M, "Delayed cerebral vasospasm and nitric oxide: review, new hypothesis, and proposed treatment," Pharmacol Ther 105(1):23-56 (2005)

Sandgren K et al., "Vasoactive intestinal peptide and nitric oxide promote survival of adult rat myenteric neurons in culture," J Neurosci Res 72(5):595-602 (2003)

Laude K et al., "NO produced by endothelial NO synthase is a mediator of delayed preconditioning-induced endothelial protection," Am J Physiol Heart Circ Physiol 284(6):H2053-60 (2003) (Epub 2003 Jan. 9)

Khan M et al., "S-Nitrosoglutathione reduces inflammation and protects brain against focal cerebral ischemia in a rat model of experimental stroke," J Cereb Blood Flow Metab 25(2):177-92 (2005)

Molloy J et al., "S-nitrosoglutathione reduces the rate of embolization in humans," Circulation 98(14):1372-5 (1998)

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998)

Zausinger V S et al., "Neurological impairment in rats after transient middle cerebral artery occlusion: a comparative study under various treatment paradigms," Brain Research 863(1-2):94-105 (2000)

Hunter A J et al., "To what extent have functional studies of ischemia in animals been useful in the assessment of potential neuroprotective agents?" Trends Pharmacol Sci 19:59-66 (1998)

Varghese et al., "Endoscopic transnasal neurolytic sphenopalatine ganglion block for head and neck cancer pain," J Laryngol Otol 115(5):385-7 (2001)

Kanner A A et al., "Serum S100beta: a noninvasive marker of blood-brain barrier function and brain lesions," Cancer 97(11):2806-13 (2003)

SUMMARY OF THE INVENTION

In some embodiments of the present invention, an electrical stimulation system is provided for the treatment of an adverse brain condition, such as an adverse cerebrovascular condition, e.g., an ischemic event. The system is configured to apply excitatory electrical stimulation to at least one "modulation target site" (MTS), as defined hereinbelow, such as a sphenopalatine ganglion (SPG). The system configures the stimulation to dilate cerebral vessels, thereby increasing cerebral blood flow (CBF) to affected brain tissue and tissue in a vicinity thereof, and/or to induce the release of one or more neuroprotective substances, such as neuromodulators (e.g., nitric oxide (NO) and/or vasoactive intestinal polypeptide (VIP)). Such increased CBF and/or release of neuroprotective substances decreases damage caused by the brain condition. The stimulation system is generally useful for treating brain ischemia, such as caused by ischemic stroke or other brain conditions.

For some applications, the system is configured to perform acute treatment of an adverse cerebrovascular event, such as ischemic stroke, by applying the stimulation within three hours of the stroke, while a significant penumbra remains. Experiments conducted by the inventors have demonstrated the efficacy of such acute treatment in an animal model. For other applications, the system is configured to perform post-acute treatment of ischemic stroke, by applying the stimulation more than three hours after the stroke, when a significant penumbra generally no longer remains. Experiments conducted by the inventors have demonstrated the efficacy of such post-acute treatment in an animal model. For still other applications, the system is configured to apply stimulation on a chronic, long-term basis, for at least one week, such as at least two weeks, at least four weeks, at least three months, or at least six months. During this chronic treatment, stimulation is typically applied intermittently, such as during one session per day. Experiments conducted by the inventors have demonstrated the efficacy of such post-acute treatment in an animal model.

In some embodiments of the present invention, the system is configured to perform staged treatment of an adverse brain event, such as a cerebrovascular event, e.g., an ischemic stroke. The system is configured to adjust at least one parameter of the applied stimulation responsively to an amount of time that has elapsed since the occurrence of the brain condition. For some applications, during a first, acute stage, the system sets the parameters of stimulation at a first, high level, which is sufficient to cause a high level of cerebral vessel dilation and/or a release of neuroprotective substances, but insufficient to induce a significant increase in permeability of the blood-brain barrier (BBB). Such stimulation is primarily intended to arrest the spreading of the initial ischemic core, such as by restoring blood flow to the penumbra in order to prevent damage to cells therein, and/or by releasing neuroprotective substances, such as NO and/or VIP. Such stimulation may also save some cells within the ischemic core, such as neuronal cells. The first stage of stimulation is typically appropriate during the period beginning at the time of the event, and ending at about 4 to 8 hours after the time of the event, such as at about 6 hours after the event. Alternatively, the first stage of stimulation is appropriate until about 24 hours after the time of the event.

During a second, rehabilitative stage, the system reduces the strength of the stimulation, and typically applies the stimulation intermittently, such as during one session per day, having a duration of between about 2 and about 3 hours. (For some applications, the session has a shorter duration, e.g., between about 0.5 and about 2 hours, or a longer duration, e.g., between about 3 and about 16 hours.) This rehabilitative level of stimulation generally continues to induce the release of neuroprotective substances, and/or maintains a slightly elevated level of blood flow to the brain. This stage of stimulation is typically applied during the period beginning at the conclusion of the first stage, and lasting at least one week, such as at least two weeks, at least one month, at least three months, or at least six months.

In the present patent application, a "modulation target site" (MTS) consists of:
- an SPG (also called a pterygopalatine ganglion);
- a nerve of the pterygoid canal (also called a vidian nerve), such as a greater superficial petrosal nerve (a preganglionic parasympathetic nerve) or a lesser deep petrosal nerve (a postganglionic sympathetic nerve);
- a greater palatine nerve;
- a lesser palatine nerve;
- a sphenopalatine nerve;
- a communicating branch between the maxillary nerve and the sphenopalatine ganglion;
- an otic ganglion;
- an afferent fiber going into the otic ganglion;
- an efferent fiber going out of the otic ganglion; or
- an infraorbital nerve.

In some embodiments of the present invention, an electrical stimulation system is configured to apply excitatory electrical stimulation to at least one MTS of a subject, and to configure the stimulation to increase CBF of the subject and/or induce the release of one or more neuroprotective substances, such as neuromodulators (e.g., nitric oxide (NO) and/or vasoactive intestinal polypeptide (VIP)), without significantly opening the BBB of the subject. For some applications, the system sets a strength of the stimulation to less than 90% of the minimum strength necessary to begin significantly opening the BBB (the "minimum BBB-opening strength"), such as less than about 80%, about 70%, or about 60% of the minimum BBB-opening strength. For some applications, the system sets the strength of stimulation to a level appropriate for long-term rehabilitation or prevention of a brain condition, such as between about 10% and about 40% of the minimum BBB-opening strength, e.g., between about 20% and about 30% of the minimum BBB-opening strength. For other applications, the system sets the strength of stimulation to a level appropriate for acute treatment of a brain event, such as at least about 20% of the minimum BBB-opening strength, e.g., at least about 50%, 60%, 70%, or 80% of the minimum BBB-opening strength.

In some embodiments of the present invention, a method for treating a brain tumor comprises: (a) during a first period of time, applying excitatory electrical stimulation to at least one MTS at a first, relatively low strength, in conjunction with administration of a chemotherapeutic drug at a first, relatively high dosage; and (b) during a second period of time after the first period, applying the stimulation at a second strength greater than the first strength, in conjunction with administration of the drug at a second dosage lower than the first dosage. Typically, stimulation at the first strength is sufficient to open the blood-tumor barrier (BTB) in the core and tissue near the core of the tumor, where the BTB has generally been damaged, but not in the periphery of the tumor, where the BBB/BTB generally remains substantially intact. Stimulation at the second strength is typically sufficient to open the BBB in the periphery of the tumor and throughout the brain.

In some embodiments of the present invention, the cerebrovascular condition is caused by a cerebrovascular incident, such as stroke, aneurysm, or an arteriovenous malformation, or by an anoxic/hypoxic/ischemic event, such as anoxic brain injury caused by near drowning, kidney failure, heart failure, chemical exposure, myocardial infarction, or electric shock. As used in the present application, including in the claims, the phrase an "adverse cerebrovascular event" includes, but is not limited to, a cerebrovascular incident, such as stroke, aneurysm, or an arteriovenous malformations, and an anoxic/hypoxic/ischemic event, such as anoxic brain injury caused by near drowning, kidney failure, heart failure, chemical exposure, myocardial infarction, or electric shock. As used in the present application, including in the claims, the phrases an "adverse cerebrovascular event" and an "adverse cerebrovascular condition" exclude from their scope Alzheimer's disease and Parkinson's disease. Nevertheless, in some embodiments of the present invention, at least some of the techniques described herein may be used for treating these two diseases.

In some embodiments of the present invention, chemical stimulation of at least one MTS is achieved by presenting chemicals, for example in a liquid or gaseous state, to an air passage of the subject, such as a nasal cavity or a throat, or in a vicinity thereof. The temporal profile and other quantitative characteristics of such chemical modulation are believed by the present inventors to have a mechanism of action that has a neuroanatomical basis overlapping with that of the electrical modulation of the MTS. For some applications, chemical-presentation techniques described herein are practiced in combination with techniques described in PCT Patent Application PCT/IL03/00338, filed Apr. 25, 2003 and/or a U.S. patent application filed Sep. 27, 2005, entitled, "Stimulation for treating and diagnosing conditions," both of which are assigned to the assignee of the present patent application and are incorporated herein by reference.

Chemicals that may increase or decrease cerebral blood flow and/or the permeability of the blood-brain barrier (e.g., via modulation of SPG-related fibers), include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol. The chemicals reach the appropriate neural structures and induce vasodilatation, vasoconstriction and/or cerebrovascular permeability changes.

In some embodiments of the present invention, chemical stimulation is applied to at least one MTS, using (a) a nasal applicator configured to deliver the stimulating chemical to an upper region of the nasal cavity, or (b) a transpalatine applicator inserted via the greater palatine canal.

In some embodiments of the present invention, stimulation of the MTS is achieved by applying mechanical stimulation to the MTS, e.g., vibration.

In some embodiments of the present invention, stimulation of at least one MTS is achieved by applying a neuroexcitatory agent to the MTS. Suitable neuroexcitatory agents include, but are not limited to, acetylcholine and urocholine. For some applications, the MTS is stimulated by applying a neuroinhibitory agent, such as atropine, hexamethonium, or a local anesthetic (e.g., lidocaine).

It is to be appreciated that references herein to specific modulation target sites are to be understood as including other modulation target sites, as appropriate.

It is further to be appreciated that insertion and modulation sites, methods of insertion and/or implantation, and parameters of modulation are described herein by way of illustration and not limitation, and that the scope of the present invention includes other possibilities which would be obvious to someone of ordinary skill in the art who has read the present patent application.

It is yet further to be appreciated that while some embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is additionally to be appreciated that whereas some embodiments of the present invention are described with respect to application of electrical currents to tissue, this is to be understood in the context of the present patent application and in the claims as being substantially equivalent to applying an electrical field, e.g., by creating a voltage drop between two electrodes.

In embodiments of the present invention, treating an adverse brain event or condition typically includes identifying that a subject is suffering from, and/or has suffered from, the brain event or condition.

There is therefore provided, in accordance with an embodiment of the present invention, apparatus for treatment, including:

one or more electrodes, configured to be applied to a site of a subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and adverse cerebrovascular condition treatment functionality, which includes a control unit configured to:

drive the one or more electrodes to apply electrical stimulation to the site during a plurality of stimulation periods which includes at least first and last stimulation periods, set an inter-period interval between initiation of the first stimulation period and initiation of the last stimulation period to be at least 24 hours, and configure the stimulation during the first and last stimulation periods to induce at least one neuroprotective occurrence selected from the group consisting of: an increase in cerebral blood flow (CBF) of the subject, and a release of one or more neuroprotective substances.

For some applications, the control unit is configured to set the inter-period interval to be no more than a maximum value. For some applications, the control unit is configured to set the inter-period interval to be no more than nine months.

In an embodiment, the control unit is configured to store a maximum total time of stimulation per each time period having a given duration, and to drive the one or more electrodes to apply the stimulation no more than the maximum total time per each time period having the given duration.

In an embodiment, the plurality of stimulation periods includes at least one second stimulation period between the first and last stimulation periods, and the control unit is configured to drive the one or more electrodes to apply the stimulation during the first, second, and last stimulation periods, and to configure the stimulation during the first, second, and last stimulation periods to induce the at least one neuroprotective occurrence.

In an embodiment, the initiation of the last stimulation period occurs simultaneously with a conclusion of the first stimulation period, and the control unit is configured to drive the one or more electrodes to apply the stimulation continuously from the initiation of the first stimulation period to a conclusion of the last stimulation period. Alternatively, the initiation of the last stimulation period occurs after a conclusion of the first stimulation period, and the control unit is configured to withhold driving the one or more electrodes to apply the stimulation during at least one non-stimulation period between the conclusion of the first stimulation period and the initiation of the last stimulation period.

For some applications, the control unit is configured to drive the one or more electrodes to apply the stimulation for between one and six hours during each of the first and last stimulation periods.

For some applications, the control unit is configured to set a strength of the stimulation during at least one of the plurality of stimulation periods to be insufficient to induce a significant increase in permeability of a blood-brain barrier (BBB) of the subject. For example, the control unit may be configured to set the strength of the stimulation during the at least one of the plurality of stimulation periods to be less than 40% of a strength that is sufficient to induce the significant increase in permeability of the BBB.

In an embodiment, the apparatus includes a user interface, which is configured to receive as input a treatment duration value, and the control unit is configured to set the inter-period interval to be equal to the inputted treatment duration value. For some applications, the control unit is configured to store a predetermined maximum treatment duration value, and to compare the inputted treatment duration value with the maximum treatment duration value.

For some applications, the control unit is configured to set the inter-period interval to be at least 48 hours. For some applications, the control unit is configured to drive the one or more electrodes to apply the stimulation non-continuously during two or more of the plurality of stimulation periods during each 24-hour period between the initiation of the first stimulation period and the initiation of the last stimulation period.

In an embodiment, the control unit is configured to set the inter-period interval to be at least one week. For some applications, the plurality of stimulation periods includes a plurality of daily stimulation periods, and the control unit is configured to drive the one or more electrodes to apply the stimulation during at least one of the daily stimulation periods on every day between the initiation of the first stimulation period and the initiation of the last stimulation period, and to configure the stimulation during the plurality of daily stimulation periods to induce the at least one neuroprotective occurrence.

For some applications, the control unit is configured to drive the one or more electrodes to apply the stimulation for at least 30 minutes every day, such as at least 60 minutes every day, between the initiation of the first stimulation period and the initiation of the last stimulation period.

For some applications, the control unit is configured to set the inter-period interval to be at least two weeks, such as at least four weeks.

For some applications, the control unit is configured to set a strength of the stimulation during at least one of the plurality of stimulation periods to be less than 40% of a strength that induces a maximum increase in CBF in the subject that is achievable by applying the stimulation. Alternatively or additionally, for some applications, the control unit is configured to set a strength of the stimulation during at least one of the plurality of stimulation periods to a level that induces less than 40% of a maximum increase in CBF in the subject that is achievable by applying the stimulation.

For some applications, the control unit is configured to drive the one or more electrodes to apply the stimulation for less than six hours during each of the first and last stimulation periods.

In an embodiment, the site includes the SPG, and the one or more electrodes are configured to be applied to the SPG. For some applications, the apparatus includes an elongated support element configured to be placed within a greater palatine canal of the subject, sized to extend from a palate of the subject to the SPG, and having a distal end, and the electrodes are fixed to the support element in a vicinity of the distal end thereof.

In an embodiment, the control unit is configured to drive the one or more electrodes to apply the stimulation during the first period at a first stimulation strength and during the last period at a second stimulation strength, and to set the second stimulation strength to be different from the first stimulation strength, such as less than or greater than the first stimulation strength.

For some applications, the adverse cerebrovascular condition treatment functionality includes stroke treatment functionality, such as ischemic stroke treatment functionality.

There is further provided, in accordance with an embodiment of the present invention, a method for treatment, including:

identifying that a subject suffers from an adverse cerebrovascular condition;

responsively to the identifying, applying electrical stimulation to a site of the subject during a plurality of stimulation periods which includes at least first and last stimulation periods, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;

setting an inter-period interval between initiation of the first stimulation period and initiation of the last stimulation period to be at least 24 hours; and configuring the stimulation during the first and last stimulation periods to induce at least one neuroprotective occurrence selected from the group consisting of: an increase in cerebral blood flow (CBF) of the subject, and a release of one or more neuroprotective substances.

In an embodiment, the adverse cerebrovascular condition includes an ischemic stroke, and identifying that the subject suffers from the condition includes identifying that the subject has experienced the ischemic stroke. Alternatively, for some applications, the condition includes an aneurysm or an arteriovenous malformation, or an anoxic brain injury caused, for example, by near drowning, kidney failure, heart failure, chemical exposure, myocardial infarction, or electric shock.

For some applications, applying the stimulation during the first and last stimulation periods includes applying the stimulation for less than six hours during each of the first and last stimulation periods.

In an embodiment, applying the stimulation includes placing an electrical stimulator in a vicinity of the site, and activating the stimulator to apply the stimulation.

In an embodiment, the condition includes an adverse cerebrovascular event, identifying that the subject suffers from the condition includes identifying that the subject has experienced the event, and applying the stimulation includes applying the stimulation beginning at least three hours after the event, such as at least six hours after the event, at least nine hours after the event, at least 12 hours after the event, or at least 24 hours after the event.

There is still further provided, in accordance with an embodiment of the present invention, apparatus for treating a subject, including:

one or more electrodes, configured to be applied to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and a control unit, configured to:

drive the one or more electrodes to apply electrical stimulation to the site, and configure the stimulation to excite nervous tissue of the site at a strength sufficient to induce at least one neuroprotective occurrence selected from the group consisting of: an increase in cerebral blood flow (CBF) of the subject, and a release of one or more neuroprotective substances, and insufficient to induce a significant increase in permeability of a blood-brain barrier (BBB) of the subject.

In an embodiment, the control unit is configured to set the strength to less than 90% of a strength sufficient to induce the significant increase in the permeability of the BBB. Alternatively or additionally, the control unit is configured to set the strength to less than 40% of a strength sufficient to induce the significant increase in the permeability of the BBB.

For some applications, the control unit is configured to set the strength to more than 50% of a strength sufficient to induce the significant increase in the permeability of the BBB.

In an embodiment, the site includes the SPG, and the electrodes are configured to be applied to the SPG. For some applications, the apparatus includes an elongated support element configured to be placed within a greater palatine canal of the subject, sized to extend from a palate of the subject to the SPG, and having a distal end, and the electrodes are fixed to the support element in a vicinity of the distal end thereof.

There is additionally provided, in accordance with an embodiment of the present invention, apparatus for treating a subject, including:

one or more electrodes, configured to be applied to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and a control unit, configured to:

drive the one or more electrodes to apply electrical stimulation to the site during at least a first period of time and a second period of time after the first period, each of the first and second periods of time having a duration of at least one minute, and configure the stimulation to excite nervous tissue of the site during the first period at a first stimulation strength and during the second period at a second stimulation strength less than the first stimulation strength, wherein the first and second stimulation strengths are sufficient to induce an increase in cerebral blood flow (CBF) of the subject.

In an embodiment, each of the first and second periods has a duration of at least one hour, and the control unit is configured to drive the one or more electrodes to apply the stimulation during the first and second periods each having the duration of at least one hour.

In an embodiment, the control unit is configured to set the first and second stimulation strengths to be insufficient to induce a significant increase in permeability of a blood-brain barrier (BBB) of the subject.

For some applications, the control unit is configured to receive an input of a point in time, and to determine the first and second time periods with respect to the point in time.

In an embodiment, the control unit is configured to apply the stimulation during a third period of time after the second period, and configure the stimulation to excite the nervous tissue during the third period at a third stimulation strength that is less than the second stimulation strength.

In an embodiment, the site includes the SPG, and the electrodes are configured to be applied to the SPG. For some applications, the apparatus includes an elongated support element configured to be placed within a greater palatine canal of the subject, sized to extend from a palate of the subject to the SPG, and having a distal end, and the electrodes are fixed to the support element in a vicinity of the distal end thereof.

There is still additionally provided, in accordance with an embodiment of the present invention, a method for treating a subject, including:

applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the stimulation to excite nervous tissue of the site at a strength sufficient to induce at least one neuroprotective occurrence selected from the group consisting of: an increase in cerebral blood flow (CBF) of the subject, and a release of one or more neuroprotective substances, and insufficient to induce a significant increase in permeability of a blood-brain barrier (BBB) of the subject.

There is yet additionally provided, in accordance with an embodiment of the present invention, a method for treating a subject, including:

applying electrical stimulation to a site of the subject during at least a first period of time and a second period of time after the first period, each of the first and second periods of time having a duration of at least one minute, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the stimulation to excite nervous tissue of the site during the first period at a first stimulation strength and during the second period at a second stimulation strength less than the first stimulation strength, wherein the first and second stimulation strengths are sufficient to induce an increase in cerebral blood flow (CBF) of the subject.

There is also provided, in accordance with an embodiment of the present invention, a method for treatment, including:

identifying that a subject has suffered from an adverse cerebrovascular event;

responsively to the identifying, applying, beginning at least three hours after the event, electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the stimulation to excite nervous tissue of the site at a strength sufficient to induce at least one neuroprotective occurrence selected from the group consisting of: an increase in cerebral blood flow (CBF) of the subject, and a release of one or more neuroprotective substances.

For some applications, applying the stimulation includes applying the stimulation beginning at least six hours after the event, such as least nine hours after the event, at least 12 hours after the event, or at least 24 hours after the event.

For some applications, configuring the stimulation includes setting the strength to be insufficient to induce a substantial increase in permeability of a blood-brain barrier (BBB) of the subject.

In an embodiment, the event includes a stroke, e.g., an ischemic stroke, and applying the stimulation includes applying the stimulation beginning at least three hours after the stroke. Alternatively, for some applications, the event includes an aneurysm or an arteriovenous malformation, or an anoxic brain injury caused, for example, by near drowning, kidney failure, heart failure, chemical exposure, myocardial infarction, or electric shock.

For some applications, applying the stimulation includes applying the stimulation intermittently.

In an embodiment, applying the stimulation includes applying the stimulation during a plurality of stimulation periods which includes at least first and last stimulation periods, wherein initiation of the first period is at least three hours after the event; and setting an inter-period interval between the initiation of the first stimulation period and initiation of the last stimulation period to be at least 24 hours, and configuring the stimulation includes configuring the stimulation during the first and last stimulation periods to induce the at least one neuroprotective occurrence.

In an embodiment, the site includes the SPG, and applying the stimulation includes applying the stimulation to the SPG. For some applications, applying the stimulation includes placing an elongated support element within a greater palatine canal of the subject, sized to extend from a palate of the subject to the SPG, and having a distal end; and applying the stimulation from a vicinity of the distal end of the support element.

There is further provided, in accordance with an embodiment of the present invention, a method for treating a subject, including:

applying, for at least 15 minutes per day during a period of at least one week, an electrical current to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the current to excite nervous tissue of the site at a strength sufficient to induce at least one of: an increase in cerebral blood flow (CBF) of the subject, and a release of one or more neuroprotective substances.

For some applications, configuring the current includes setting the strength to be less than 40% of a strength that induces a maximum increase in CBF in the subject that is achievable by applying the current. Alternatively or additionally, configuring the current includes setting the strength to a level that induces less than 40% of a maximum increase in CBF in the subject that is achievable by applying the current.

For some applications, applying the current includes applying the current for less than 6 hours per day.

For some applications, applying the current includes implanting an electrical stimulator in a vicinity of the site, and activating the stimulator to apply the current.

In an embodiment, configuring the current includes setting the strength to be insufficient to induce a significant increase in permeability of a blood-brain barrier (BBB) of the subject. For some applications, setting the strength includes setting the strength to be less than 40% of a strength that is sufficient to induce the significant increase in permeability of the BBB.

In an embodiment, the site includes the SPG, and applying the current includes applying the current to the SPG. For some applications, applying the current includes: placing an elongated support element within a greater palatine canal of the subject, sized to extend from a palate of the subject to the SPG, and having a distal end; and applying the current from a vicinity of the distal end of the support element.

For some applications, applying the current includes applying the current for at least 30 minutes per day during the period of at least one week, such as for at least 60 minutes per day during the period of at least one week.

There is additionally provided, in accordance with an embodiment of the present invention, a method for treating a brain tumor of a subject, including:

administering a chemotherapeutic drug to the subject;

during a first period of time during which the drug is at a first level in a systemic circulation of the subject, applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve, and configuring the stimulation to excite nervous tissue of the site at a first strength sufficient to induce an increase in permeability of a blood-tumor barrier (BTB) of the subject; and during a second period of time during which the drug is at a second level in the systemic circulation, the second level lower than the first level, applying the stimulation to the site, and configuring the stimulation to excite the nervous tissue at a second strength that is greater than the first strength.

In an embodiment, configuring the stimulation during the first period includes setting the first strength to be insufficient to induce a significant increase in permeability of a blood-brain barrier (BBB) of the subject. Alternatively or additionally, configuring the stimulation during the second period includes setting the second strength to be sufficient to induce a significant increase in permeability of a BBB of the subject. Further alternatively or additionally, configuring the stimulation during the first and second periods includes setting the first strength to be insufficient to induce a significant increase in permeability of a BBB of the subject, and the second strength to be sufficient to induce the significant increase in the permeability of the BBB.

In an embodiment, the site includes the SPG, and applying the stimulation includes applying the stimulation to the SPG. For some applications, applying the stimulation during the first and second periods includes: placing an elongated support element within a greater palatine canal of the subject, sized to extend from a palate of the subject to the SPG, and having a distal end; and applying the stimulation from a vicinity of the distal end of the support element.

There is yet additionally provided, in accordance with an embodiment of the present invention, a method for treating a brain tumor of a subject, including:

administering a chemotherapeutic drug to the subject;

applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve; and configuring the stimulation to excite nervous tissue of the site at a strength sufficient to induce an increase in permeability of a blood-tumor barrier (BTB) of the subject, but insufficient to induce a substantial increase in permeability of a blood-brain barrier (BBB) of the subject.

In an embodiment, the site includes the SPG, and applying the stimulation includes applying the stimulation to the SPG. For some applications, applying the stimulation includes: placing an elongated support element within a greater palatine canal of the subject, sized to extend from a palate of the subject to the SPG, and having a distal end; and applying the stimulation from a vicinity of the distal end of the support element.

The present invention will be more fully understood from the following detailed description of the embodiments thereof, taken together with the drawings, in which:

BRIEF DESCRIPTION OF THE DRAWINGS

FIG. 3 is a graph illustrating electrical stimulation protocols, in accordance with an embodiment of the present invention;

FIG. 4 is a graph showing a rehabilitation protocol for treating stroke, in accordance with an embodiment of the present invention;

FIGS. 9A-C are graphs showing the results of in vivo experiments assessing the effect of SPG stimulation performed three hours following stroke, measured in accordance with respective embodiments of the present invention;

FIG. 10 is a graph showing results of an in vivo experiment assessing the effect of rehabilitative SPG stimulation, measured in accordance with an embodiment of the present invention;

FIGS. 11A-C are graphs showing results of an in vivo experiment assessing the effect of rehabilitative SPG stimulation, measured in accordance with an embodiment of the present invention;

FIGS. 12A-H are graphs showing results of an in vivo experiment assessing the effect of long-term rehabilitative SPG stimulation, measured in accordance with an embodiment of the present invention; and FIG. 13 is a graph showing a protocol for treating a brain tumor, in accordance with an embodiment of the present invention.

DETAILED DESCRIPTION OF THE INVENTION

Figure 1:
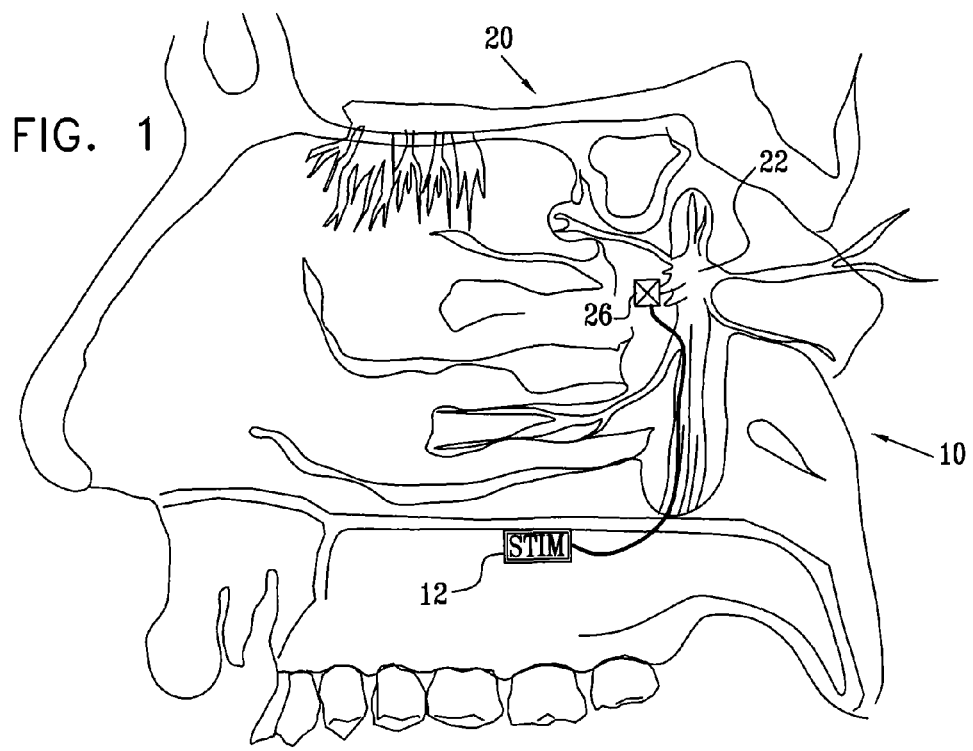
FIG. 1 is a schematic pictorial view of an electrical stimulation system comprising an implantable stimulator for stimulation of an MTS, in accordance with an embodiment of the present invention.

FIG. 1 is a schematic pictorial view of an electrical stimulation system 10 comprising an implantable stimulator 12, for stimulation of a "modulation target site" (MTS), as defined hereinabove, such as a sphenopalatine ganglion (SPG) 22, in accordance with an embodiment of the present invention. In FIG. 1, a human nasal cavity 20 is shown, and stimulator 12 is implanted between the hard palate and the mucoperiosteum (not shown) of the roof of the mouth. Branches of parasympathetic neurons coming from SPG 22 extend to the middle cerebral and anterior cerebral arteries (not shown). Typically, one or more relatively short electrodes 26 extend from stimulator 12 to contact or to be in a vicinity of an MTS, such as SPG 22.

For some applications, stimulator 12 is implanted on top of the bony palate, in the bottom of the nasal cavity. Alternatively or additionally, the stimulator is implanted at the lower side of the bony palate, at the top of the oral cavity. In this instance, one or more flexible electrodes 26 originating in the stimulator are passed through the palatine bone or posterior to the soft palate, so as to be in a position to stimulate the SPG or another MTS. Further alternatively or additionally, the stimulator may be directly attached to the SPG and/or to another MTS.

For some applications, stimulator 12 is delivered to a desired point within nasal cavity 20 by removably attaching stimulator 12 to the distal end of a rigid or slightly flexible introducer rod (not shown) and inserting the rod into one of the patient's nasal passages until the stimulator is properly positioned. As appropriate, the placement process may be facilitated by fluoroscopy, x-ray guidance, fine endoscopic surgery (FES) techniques or by any other effective guidance method known in the art, or by combinations of the aforementioned. Typically, skin temperature and/or cerebral blood flow (CBF) is measured concurrently with insertion. CBF may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring CBF.

For some applications, stimulator 12 is implanted using techniques described in U.S. patent application Ser. No. 10/535,024, filed Dec. 27, 2005, entitled, "Surgical tools and techniques for stimulation," which is assigned to the assignee of the present application and is incorporated herein by reference, and/or in the above-mentioned PCT Publication WO 04/043218. For some applications, techniques described herein are performed in combination with apparatus and/or methods that are described in U.S. patent application Ser. No. 11/349,020, filed Feb. 7, 2006, entitled, "SPG stimulation via the greater palatine canal," which is assigned to the assignee of the present application and is incorporated herein by reference.

Figure 2:
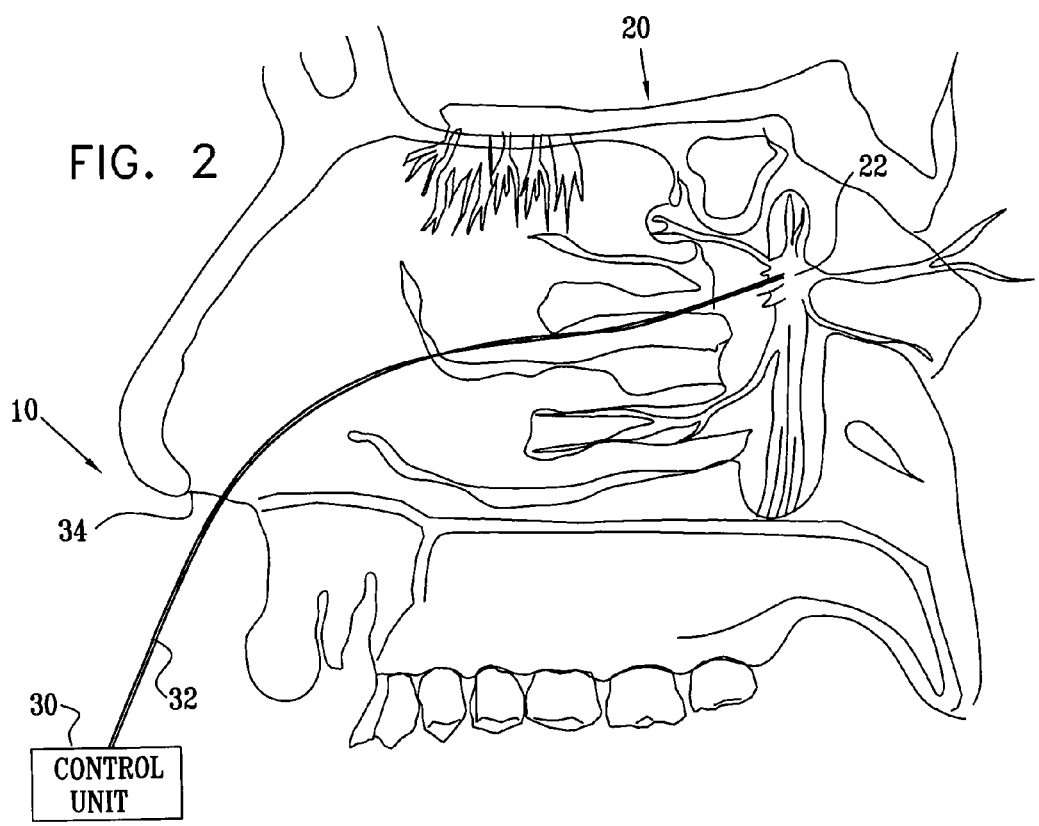
FIG. 2 is a schematic pictorial view of another stimulator for stimulation of an MTS, in accordance with an embodiment of the present invention.

FIG. 2 is a schematic illustration of a stimulator control unit 30 positioned external to a patient's body, in accordance with an embodiment of the present invention. At least one flexible electrode 32 typically extends from control unit 30, through a nostril 12 of the patient, and to a position within the nasal cavity that is adjacent to SPG 22.

In an embodiment of the present invention, techniques described herein are performed in conjunction with techniques described in US Patent Application Publication 2004/0220644, which is assigned to the assignee of the present application and is incorporated herein by reference. For example, the substantially rigid support element described therein may be initially quickly inserted into the stimulation site for acute treatment, and an implantable stimulator 12 may be subsequently implanted for longer-term treatment.

It is to be understood that electrodes 26 (FIG. 1) and 32 (FIG. 2) may each comprise one or more electrodes, e.g., two electrodes, or an array of microelectrodes. For applications in which stimulator 12 comprises a metal housing that can function as an electrode, typically one electrode 26 is used, operating in a monopolar mode. Regardless of the total number of electrodes in use, typically only a single or a double electrode extends to SPG 22. Other electrodes 26 or 32 or a metal housing of stimulator 12 are typically temporarily or permanently implanted in contact with other parts of nasal cavity 20.

Each of electrodes 26 and/or 32 typically comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is typically insulated with a physiologically-acceptable material such as polyethylene, polyurethane, or a co-polymer of either of these. The electrodes are typically spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate.

Reference is made to FIG. 3, which is a graph 100 illustrating electrical stimulation protocols, in accordance with an embodiment of the present invention. Excitatory stimulation of an MTS (e.g., the SPG) induces changes in CBF, induces the release of one or more neuroprotective substances, such as neuromodulators (e.g., nitric oxide (NO) and/or vasoactive intestinal polypeptide (VIP)), and/or modulates permeability of the blood-brain barrier (BBB). The inventors have found that excitatory stimulation of an MTS at at least a minimum threshold strength increases CBF, and that the increase in CBF is related to the strength of the stimulation. The inventors have also found that at a sufficiently high strength, such stimulation modulates the permeability of the BBB, in addition to increasing CBF.

"Strength," as used in the present application, including the claims, means a total charge applied to an MTS in a given time period, e.g., one minute, one hour, or one day. Strength is increased or decreased by changing one or more parameters of the applied stimulation, such as the amplitude, number of cycles in a given time period, frequency, pulse width, or duty cycle (e.g., ratio of "on" to "off" time within a given cycle), as described hereinbelow in greater detail.

The y-axis of graph 100 indicates the strength of the stimulation of an MTS. The strength of the stimulation is determined by the values of the parameters of the stimulation, such as voltage, current, frequency, cycles per time period, and duty cycle. Stimulation at at least a minimum CBF-increasing strength 102 increases CBF. Stimulation at such a strength also typically induces the release of one or more neuroprotective substances, such as NO and/or VIP. A maximum CBF-increasing strength 106 is the strength at which CBF is maximally increased, i.e., further increases in strength do not further increase CBF. The BBB is opened, i.e., the permeability of the BBB to larger molecules or substances that do not cross the intact BBB is significantly increased, by stimulation having a strength in a range 108 between a minimum BBB-opening strength 110 and maximum BBB-opening strength 112 (beyond which increased strength does not result in additional opening of the BBB). Although minimum BBB-opening strength 110 is shown in graph 100 as being greater than maximum CBF-increasing strength 106, this is not necessarily the case.

In the present application, including the claims, stimulation of an MTS is considered capable of inducing a "significant" increase in the permeability of the BBB if the stimulation is capable of inducing at least one of the following:

(a) an increase in concentration of Evans blue (EB) in brain tissue of a subject, such as a rat, of at least 100% compared to a baseline concentration measured in a control rat. To determine the increase, permanent middle cerebral artery occlusion (pMCAO) is induced in the rat, such as using techniques described hereinbelow with reference to FIG. 6. Three hours after pMCAO, stimulation is applied to the MTS, and a bolus of EB 2% at 1 ml per kg body weight of the rat is administered intravenously. The rat is sacrificed one hour after application of the stimulation and administration of the EB. To determine the baseline concentration, pMCAO is induced in a control rat, three hours after pMCAO an identical EB bolus is administered intravenously, but no stimulation is applied, and the control rat is sacrificed one hour after the administration of the EB; and (b) a serum S100beta level of the subject (indicative of clearance of the protein from the brain into the systemic circulation), at a measurement time 45 minutes after initiation of MTS stimulation, that is at least 30% greater than a serum S100beta level of the subject measured at the beginning of the MTS stimulation.

Although the above are indications of the "significance" of an increase in permeability of the BBB, use of the apparatus and performance of the methods described and claimed herein typically do not include measuring any of these indications. In particular, indication (a) is generally only possible to measure in an animal model; if it were desired to conduct a human experiment, different techniques would likely be used, such as measuring the concentration in the brain of a radioactive isotope that is normally excluded by the BBB.

For some applications, it is desirable to apply stimulation to an MTS, and configure the stimulation to have a strength that induces an increase in permeability of the BBB that is even lower than a "significant" increase, as defined above. Such a "sub-significant" increase in permeability of the BBB is considered to occur if the stimulation is capable of inducing at least one of the following: (i) an increase in concentration of EB, under the conditions defined in indication (a) above, of at least 20%, such as at least 30%, e.g., at least 50%; and (ii) a serum S100beta level, under the conditions defined in indication (b) above, that is at least 10%, e.g., at least 20%, greater than the level of the subject measured at the beginning of the MTS stimulation.

For some applications, it is useful to define increased CBF as a percentage increase in CBF over a baseline level of CBF, which increase has at least a certain duration, e.g., at least 5 minutes. Typically, the baseline CBF level is either: (a) a normal baseline level for a subject, i.e., prior to an adverse brain event, such as a cerebrovascular event, e.g., a stroke, or (b) a post-event baseline level, prior to stimulation using the techniques described herein, and, optionally, prior to other treatment of the event. CBF is typically expressed as volume of blood flow per time per mass of the subject, e.g., ml/min/100 g. For some applications, increased CBF is expressed as an area under the curve (AUC) of CBF with respect to baseline over a certain time interval.

In an embodiment of the present invention, electrical stimulation system 10 is configured to apply excitatory electrical stimulation to at least one MTS of a subject, and to configure the stimulation to increase CBF of the subject and/or induce the release of neuroprotective substances, without substantially opening the BBB of the subject. In other words, the system sets the strength of stimulation equal to less than minimum BBB-opening strength 110, such as less than 90% of minimum BBB-opening strength 110, e.g., less than 80%, 70%, or 60% of minimum BBB-opening strength 110. For some applications, the system is configured to increase CBF of the subject and/or induce the release of neuroprotective substances without increasing the permeability of the BBB to a level that produces a measurably-harmful clinical effect for the subject.

For some applications, system 10 sets an acute strength 122 equal to a level appropriate for treatment of an acute condition, such as an adverse brain event (e.g., a cerebrovascular event), for which increased CBF and/or release of neuroprotective substances is beneficial, but for which opening the BBB is not indicated. For example, the system may set acute strength 122 equal to at least about 20% of minimum BBB-opening strength 110, e.g., at least about 50%, 60%, 70%, or 80% of minimum BBB-opening strength 110.

In an embodiment of the present invention, system 10 is used for rehabilitative treatment after an adverse brain event, such as a cerebrovascular event, e.g., a stroke, or for rehabilitative treatment of a non-acute cerebrovascular condition. Such rehabilitative stimulation induces the release of neuroprotective substances and/or maintains a slightly elevated level of blood flow, typically over an extended period of time, such as at least 24 hours, at least one week, at least two weeks, at least four weeks, or at least three months. As a result, such stimulation typically rehabilitates damaged tissue, improves perfusion of the rehabilitating brain, and/or accelerates angiogenesis. (See, for example, the above-mentioned article by Zhang R et al. (2001), which reports that NO donors administrated 24 hours after stroke significantly increased angiogenesis in the ischemic boundary regions.) For some applications, the system is configured to apply such rehabilitative stimulation intermittently, such as during one session per day, having a duration of between 1 minute and 6 hours, such as at least 5 minutes or at least 15 minutes, or between 2 and 4 hours, e.g., about 3 hours or about 6 hours, or more than 6 hours. Alternatively, the system is configured to apply such stimulation generally constantly, i.e., 24 hours per day. Further alternatively, the rehabilitative stimulation is applied less frequently than every day, such as once every other day (e.g., at least one minute during every 48 hours), or more frequently than once per day, such as during two sessions per day. For some applications, such stimulation is applied beginning at least one hour after the adverse brain event, such as a cerebrovascular event, e.g., a stroke, such as beginning at least 3 hours, at least 6 hours, at least 9 hours, at least 12 hours, at least 24 hours, or at least 48 hours after the brain event. For some applications, NO released by stimulation at rehabilitation strength 122 is of particular neuroprotective benefit during rehabilitation.

For some applications, such rehabilitative stimulation is applied during a plurality of stimulation periods which includes at least first and last stimulation periods. System 10 sets an inter-period interval between initiation of the first period and initiation of the last period to be at least 24 hours. For example, the first stimulation period may occur from 1:00 P.M. to 4:00 P.M. on a Monday, and the last stimulation period may occur from 1:00 P.M. to 4:00 P.M. on a Tuesday of the same week. Optionally, stimulation is applied during at least one additional stimulation period between the first and last periods. For example, stimulation may be additionally applied from 1:00 A.M. to 4:00 A.M. on the Tuesday. For some applications, the first period concludes simultaneously with the initiation of the last period, i.e., the stimulation is applied constantly from the beginning of the first period until the conclusion of the last period. For example, the stimulation may be applied constantly from 1:00 P.M. on Monday, January 1 to 4:00 P.M. on Tuesday, January 2, or constantly from 1:00 P.M. on Monday, January 1 to 4:00 P.M. on Monday, January 29. Alternatively, the initiation of the last stimulation period occurs after a conclusion of the first stimulation period, such that the stimulation is not applied during at least one non-stimulation period between the conclusion of the first stimulation period and the initiation of the last stimulation period.

For some applications, the system sets the inter-period interval to be at least 48 hours, such as at least one week, at least two weeks, or at least four weeks. When using such greater inter-period intervals, the system typically, but not necessarily, applies stimulation during at least several additional stimulation periods between the first and last stimulation periods. For some applications, such additional stimulation periods may include a plurality of daily stimulation periods, applied on every day between the initiation of the first stimulation period and the initiation of the last stimulation period. For example, the first stimulation period may occur from 1:00 P.M. to 4:00 P.M. on Monday, January 1, the last stimulation period may occur from 1:00 P.M. to 4:00 P.M. on Monday, January 8, and the additional daily stimulation periods may occur from 1:00 P.M. to 4:00 P.M. on each day from Tuesday, January 2 through Sunday, January 7, inclusive. For some applications, stimulation is applied for at least 30 minutes every day (e.g., at least 60 minutes every day) between the initiation of the first stimulation period and the initiation of the last stimulation period. For some applications, stimulation is applied during a plurality of non-continuous stimulation periods during each 24-hour period between the initiation of the first stimulation period and the initiation of the last stimulation period. For example, the first stimulation period may occur from 1:00 P.M. to 4:00 P.M. on Monday, the last stimulation period may occur from 1:00 P.M. to 4:00 P.M. on Wednesday, and stimulation may be applied during additional stimulation periods from (a) 1:00 A.M. to 4:00 A.M. on Tuesday, (b) from 1:00 P.M. to 4:00 P.M. on Tuesday, and (c) from 1:00 A.M. to 4:00 A.M. on Wednesday, such that stimulation is applied during two stimulation periods during the 24-hour period from 1:00 P.M. on Monday to 1:00 P.M. on Tuesday, and during two stimulation periods during the 24-hour period from 1:00 P.M. on Tuesday to 1:00 P.M. on Wednesday.

For some applications, the system is configured to set the inter-period interval to be no more than a maximum value, such as three, six, nine, or twelve months. For some applications, the system comprises a user interface, which enables a healthcare worker to enter a value for the inter-period interval. The system typically rejects values that are greater than the maximum value, such as by requiring the healthcare worker to enter another value, or by using the maximum value instead of the entered value. Alternatively, the system notifies the healthcare worker if the entered value is greater than the maximum value; optionally, the system allows the healthcare worker to override the notification.

For some applications, the system is configured to store a maximum total time of stimulation per each time period having a given duration, and to apply the stimulation no more than the maximum total time per each time period having the given duration. For example, the given duration of each time period may be 24 hours. Typical values for the maximum total time of stimulation per 24-hour period include one hour, three hours, six hours, ten hours, and twelve hours. For some applications, the maximum total time of stimulation is predetermined, e.g., by the manufacturer of the system, while for other applications, a healthcare worker enters the maximum total time of stimulation into the system.

As used in the present application, including the claims, a "stimulation period" includes an entire period during which stimulation is applied, even though current is applied to the site only during a portion of the period, because of the duty cycle, on/off periods, and/or frequency of the current, for example.

For some applications, system 10 sets the strength of stimulation during such long-term rehabilitation to a rehabilitation strength 120, such as between about 10% and about 40% of minimum BBB-opening strength 110, e.g., between about 20% and about 30% of minimum BBB-opening strength 110, or such as between about 10% and about 40% of maximum CBF-increasing strength 106, e.g., between about 20% and about 30% of maximum CBF-increasing strength 106. Alternatively or additionally, system 10 sets rehabilitation strength 120 to a level that causes an increase in CBF equal to less than about 40% of a maximum CBF increase that system 10 is capable of inducing.

In an embodiment of the present invention, system 10 sets the strength of stimulation to a preventive strength appropriate for preventing an occurrence of a brain event, typically a secondary brain event, e.g., a secondary stroke. For example, such strength may be between about 5% and about 50% of the minimum BBB-opening strength 110. For some applications, NO released by stimulation at the preventive strength is of particular neuroprotective benefit during prevention, and has an anti-thrombolytic, vasodilatory, and/or anti-inflammatory effect.

In an embodiment of the present invention, system 10 is configured to treat a complication of subarachnoid hemorrhage (SAH), such as a cerebral vasospasm. The currently-preferred conventional treatment for SAH includes a surgical procedure in which a medical vehicle is used to treat the SAH. The medical vehicle may comprise, for example: (a) a tool for treating the SAH such as by clipping the aneurysm that caused the SAH, and/or (b) a pharmaceutical treatment. However, the presence of blood in the subarachnoid space sometimes causes increased sensitization of large cerebral arteries, resulting at a later time in cerebral vasospasms. These late-onset vasospasms, in turn, cause brain ischemia and often irreversible damage (see the above-mentioned article by Van Gijn J et al.). Therefore, the stimulation of the MTS of this embodiment of the present invention is typically applied in conjunction with such a treatment (e.g., before, during or after the treatment), typically to the SPG, in order to counteract the reduced CBF sometimes caused by blood passage into the subarachnoid space.

Typically, for treating the complication of SAH, system 10 configures the stimulation to increase CBF of the subject and/or induce the release of neuroprotective substances, without substantially opening the BBB of the subject. Typically, system 10 is configured to set the strength of stimulation to at least acute strength 122, but no more than maximum CBF-increasing strength 106, so as not to substantially open the BBB. For some applications, the stimulation of the MTS is initiated at a time after the treatment when the hemorrhage has already been substantially reduced (at which time, in the absence of MTS stimulation, CBF is frequently reduced below desired levels). Alternatively, the stimulation of the MTS is initiated prior to this point, but generally has its strongest elevating effect on CBF once the hemorrhage has been substantially reduced.

Reference is again made to FIG. 3. In an embodiment of the present invention, electrical stimulation system 10 is configured to apply staged treatment of a brain event, such as an ischemic event (e.g., a stroke). The system configures the stimulation to dilate cerebral vessels, thereby increasing CBF to affected brain tissue and tissue in a vicinity thereof, and/or to induce the release of one or more neuroprotective substances, such as neuromodulators (e.g., nitric oxide (NO)

and/or vasoactive intestinal polypeptide (VIP)). Such increased CBF and/or release of neuroprotective substances decrease damage caused by the brain event. The system is typically configured to adjust at least one parameter of the applied stimulation responsively to an amount of time that has elapsed since the occurrence of the brain event. For some applications, system 10 calculates the elapsed time responsively to an estimated time of occurrence of the brain event, which is entered into the system by a healthcare worker, typically early in the treatment of the event. In these applications, the system typically automatically progresses from stage to stage based on the elapsed time from the occurrence of the event. Alternatively, for some applications, a healthcare worker manually selects the stages.

System 10 is typically configured to apply the stimulation in two or more stages. For some applications, during a first, acute stage 130, the system sets the parameters of stimulation to acute strength 122, which is sufficient to cause a high level of cerebral vessel dilation and/or a release of neuroprotective substances, but insufficient to substantially open the BBB. Such stimulation is primarily intended to arrest the spreading of the initial ischemic core, such as by restoring blood flow to the penumbra in order to prevent damage to cells therein, and/or by releasing neuroprotective substances, such as NO and/or VIP. Such stimulation may also save some cells within the ischemic core, such as neuronal cells. The first stage of stimulation is typically appropriate during the period beginning at the time of the event, and ending at about 4 to 8 hours after the time of the event, such as at about 6 hours after the event. Alternatively, the first stage of stimulation is appropriate until about 24 hours after the time of the event. (See, for example, the above-cited articles by Davis S M et al. and Phan T G et al.) For some applications, VIP released by stimulation at acute strength 122 is of particular neuroprotective benefit. For some applications, hypoperfused areas of the brain are identified, such as by using MRI or PET, which can potentially be saved using the stimulation techniques described herein.

During a second, rehabilitative stage 136, system 10 reduces the strength of the stimulation to rehabilitation strength 120, and typically applies the stimulation intermittently, such as during one session per day, having a duration of between 1 minute and 6 hours, such as between 2 and 4 hours, e.g., about 3 hours, or more than 6 hours. This rehabilitative level of stimulation continues to induce the release of neuroprotective substances, and/or maintains a slightly elevated level of blood flow. This stage of stimulation is typically applied during the period beginning at the conclusion of acute stage 130, and lasting at least one week, such as at least two weeks, at least one month, at least three months, or at least six months. Alternatively, the rehabilitative stimulation is applied generally constantly, i.e., 24 hours per day. Further alternatively, the rehabilitative stimulation is applied less frequently than every day, such as once every other day, or more frequently than once per day, such during two sessions per day.

For some applications, system 10 is configured to apply stimulation during an additional, post-acute stage 132, between acute stage 130 and rehabilitative stage 136. During post-acute stage 132, the system reduces the strength of the stimulation to a post-acute strength 134, between acute strength 122 and rehabilitation strength 120. This post-acute strength is sufficient to maintain an increased level of blood flow to and/or release of neuroprotective substances to the ischemic core and the penumbra. The lower strength is less likely to cause potential side effects, such as aneurysm, that might occur if the system maintained the higher level of stimulation of the first stage. Typically, post-acute strength 134 is equal to between about 20% and 70% of minimum BBB-opening strength 110, such as between about 40% and 60%. Post-acute stage 132 typically begins at the conclusion of acute stage 130, and ends at about 16 to 30 hours after the time of the event, such as about 24 hours after the event.

The following table shows exemplary parameter ranges for some of the stimulation strengths and treatment protocols described hereinabove.

TABLE 1

| Indication | Signal amplitude | | Hz | Pulse width (μsec) | No. of Cycles per hour | Cycle on/off time (sec) |
|---|---|---|---|---|---|---|
| Acute treatment | 0.5-10 | mA | 10-30 | 100-500 | 1-10 | 60/12, 4/15, 30/60 |
| Rehabilitation | 0.5-10 | mA | 10-30 | | | |
| Prevention of recurrence | 0.5-10 | mA | 10-30 | | | |
| Minimum BTB | 1-3.5 | V | 10-30 | 100-500 | 1-100 | 45/45, 45/90, 90/60, 4/15, 2/8 |
| Minimum BBB | 1-4 | V | 10-30 | | | |
| Maximum BBB | 3.5-8 | V | 10-50 | | | |

As indicated in Table 1, for some applications system 10 provides stimulation by applying a plurality of cycles of stimulation, each cycle including an "on" period (e.g., between 2 and 90 seconds) followed by an "off" period (e.g., between 8 and 90 seconds). Such cycles are applied a certain number of times per hour, typically spaced evenly throughout the hour. For example, if the cycles are applied four times per hour, the four cycles may be applied at the beginning of the hour, 15 minutes into the hour, 30 minutes into the hour, and 45 minutes into the hour, respectively. For some applications, each stimulation is applied in sets of two or more cycles. For example, if the stimulation is applied four times per hour, a set of two cycles may be applied at the beginning of the hour, 15 minutes into the hour, 30 minutes into the hour, and 45 minutes into the hour, respectively.

For some applications, in order to apply different strengths for the different brain event protocols (acute treatment, post-acute treatment, rehabilitation, and prevention of recurrence of the event), system 10 changes the amplitude of the applied signal and/or the number of cycles per hour. Alternatively or additionally, the system changes the frequency, pulse width, duration of the "on" periods, duration of the "off" periods, ratio of duration of the "on" to the "off" periods, number of cycles per set of cycles, or at least one other parameter of the stimulation.

Nitric oxide (NO) influences infarct size after focal cerebral ischemia and also regulates neurogenesis in the adult brain. These observations suggest that therapeutic approaches to stroke that target NO signaling may provide neuroprotection and also enhance brain repair through cell replacement (see Zhang R et al. (2001) and Sun Y et al., cited hereinabove). Utilizing a rat model, Zhang R et al. (2001) demonstrated that treatment of stroke with nitric oxide (NO) donors reduces functional neurological deficits. Zhang F et al. (cited hereinabove) demonstrated that NO donors increase CBF to the ischemic territory and reduce the tissue damage resulting from focal ischemia. The protective effect may result from an increase in CBF to the ischemic territory, probably the ischemic penumbra. NO and VIP have been found to be potent neuroprotectants in cell culture models (see the above-mentioned article by Sandgren K et al.). Khan M et al. (cited hereinabove), using S-nitrosothiols, a nitric oxide (NO) donor, demonstrated that administration of NO provided neuroprotection in a rat model of focal cerebral ischemia. Ziche M et al. (cited hereinabove) discuss the role of NO, as a factor responsible for vasodilation, in physiological and pathological angiogenesis. The inventors hypothesize that the release of NO induced by the stimulation techniques described herein may have therapeutic benefits, even if such stimulation is applied beginning several hours, or even several days, after the stroke.

In an embodiment of the present invention, stimulation during acute stage 130 and/or post-acute stage 132 is performed using a needle-like electrode, which is inserted, using a simple procedure, into a subject recently admitted to a hospital after a stroke. For example, the device described with reference to FIGS. 1-4B and/or FIGS. 17A-C of the above-mentioned U.S. patent application Ser. No. 11/349,020 may be used for the acute and/or post-acute stages. Upon completion of one or both of these stages, and/or stabilization of the subject, the needle-like electrode is removed, and a longer-term stimulator is implanted and used for rehabilitative stage 136 and/or the preventive stage. For example, the device described with reference to FIGS. 5A-D, 12-14B, and/or 17A-C of the '020 application may be used for the rehabilitative and/or preventive stages.

Reference is made to FIG. 4, which is a graph 150 showing a rehabilitation protocol for treating stroke, in accordance with an embodiment of the present invention. In accordance with this protocol, system 10 is configured to alternatingly apply stimulation at a first, rehabilitative level of strength, and at a second BBB-opening level of strength in conjunction with administration of a drug for rehabilitation from stroke. For example, the drug may include a growth factor, such as BDNF, GDNF, or NGF. Typically, the first rehabilitative level is rehabilitation strength 120, described hereinabove with reference to FIG. 3, and the second BBB-opening level falls within BBB-opening range 108, such as maximum BBB-opening strength 112, described hereinabove with reference to FIG. 3. System 10 is typically configured to apply the rehabilitative stimulation intermittently, such as during one session per day, having a duration of between about 1 and about 6 hours, such as between about 2 and about 4 hours day, e.g., about 3 hours. Alternatively, the rehabilitative stimulation is applied less frequently than every day, such as once every other day, or more frequently than once per day, such as during two sessions per day.

System 10 is typically configured to apply the BBB-opening stimulation intermittently, such as for between about 0.5 and about 1 hour per day, or for between about 3 and about 6 hours per day, e.g., about 4 hours per day. Alternatively, the BBB-opening stimulation is applied less frequently than every day, such as once every other day, or more frequently than once per day, such as twice per day, or 24 times per day. The drug administered in conjunction with applying the BBB-opening stimulation is typically administered systematically, before and/or during application of the BBB-opening stimulation. For some applications, the rehabilitative stimulation is applied immediately before or after the BBB-opening stimulation (as shown in FIG. 4), while for other applications the rehabilitative and BBB-opening stimulations are applied non-contiguously (not shown in FIG. 4).

Figure 5:
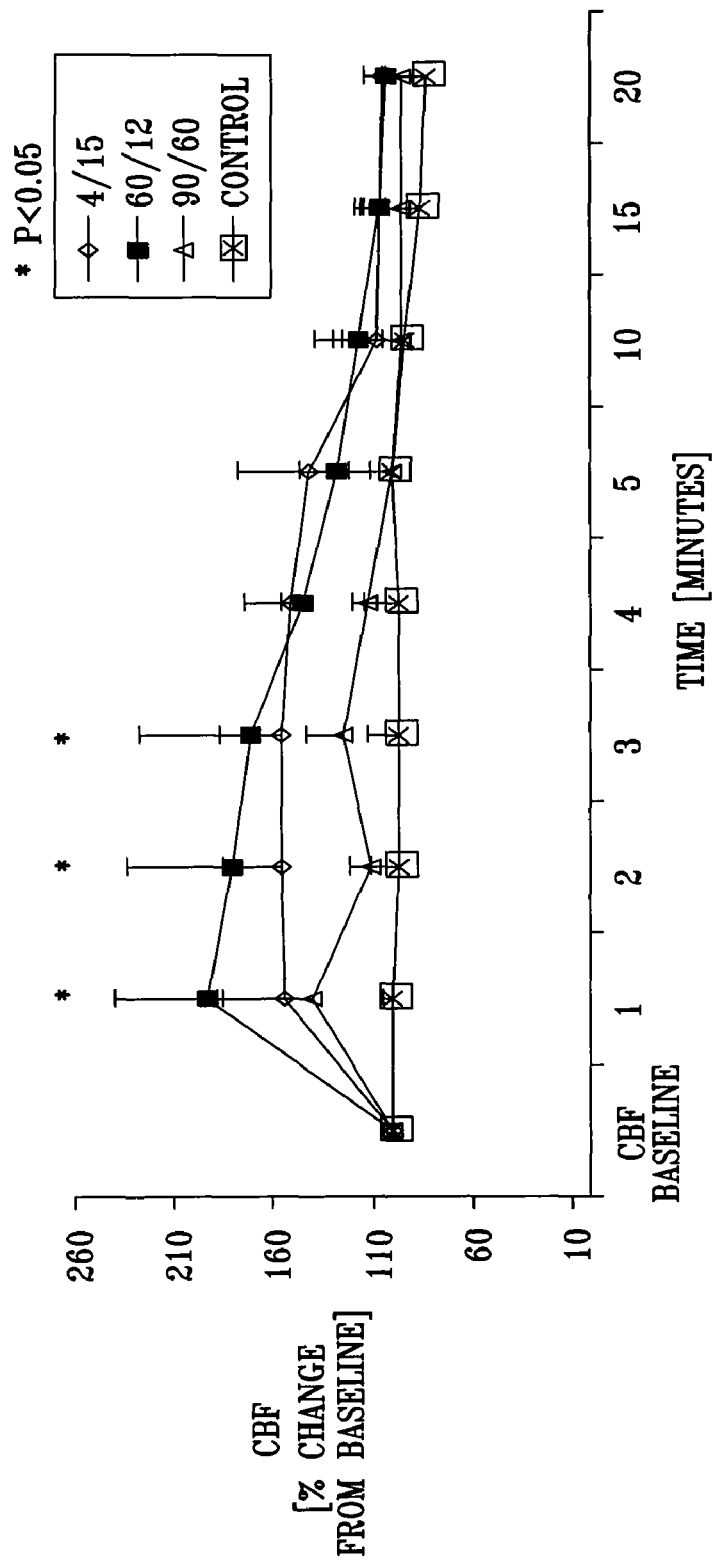
FIG. 5 is a graph showing changes in cerebral blood flow (CBF) vs. baseline using three different SPG stimulation protocols, measured in accordance with an embodiment of the present invention.

Reference is made to FIG. 5, which is a graph showing changes in CBF vs. baseline using three different SPG stimulation protocols, measured in accordance with an embodiment of the present invention. 16 naive rats were anesthetized with a ketamine-xylazine combination, and a plastic holder was affixed to the skull for CBF measurement. A bipolar electrode was brought into contact with the SPG and connected to a controller. The SPG was stimulated for five minutes beginning after CBF stabilization, using the following signal parameters: 3.5 volts, 10 Hz, and a 500 μsec pulse width. The rats were divided into four groups, one of which served as a control, and the other three received stimulation having different duty cycles: 4 seconds on/15 seconds off, 60 seconds on/12 seconds off, and 90 second on/60 second off. As can be seen in FIG. 5 and in Table 2 below, CBF significantly increased in two of the stimulation groups (4/15 and 60/12) vs. CBF baseline. The maximum increase in CBF vs. baseline (193%) was observed in the 60/12 stimulation group after two minutes of SPG stimulation. CBF in this group remained elevated even 10-15 minutes after termination of SPG stimulation. The minimum increase in CBF vs. baseline (141%) was observed in the 90/60 stimulation group. It is clear from these results that SPG stimulation at the described parameters significantly increases CBF, and that such increase was stable at 10 minutes following SPG stimulation.

TABLE 2

| Group | CBF at 2 minutes [% change from baseline] |
|---|---|
| 4/15 (n = 5) | 157 |
| 60/12 (n = 6) | 193 |
| 90/60 (n = 5) | 141 |

Reference is made to FIGS. 6-11C, which are graphs showing in vivo experimental results, measured in accordance with respective embodiments of the present invention. These animal experiments were performed to test the efficacy of the SPG stimulation techniques described hereinabove for treating stroke. The experiments described with reference to FIGS. 6-11C used a rat middle cerebral artery occlusion (MCAO) model of stroke. As described in detail hereinbelow, these experiments demonstrated that:

SPG stimulation starting three hours following MCAO occlusion significantly improved cerebral blood flow (CBF), decreased infract size, and improved neuromuscular function;

SPG stimulation reduced mortality;

SPG stimulation for one or three hours per day for three days, beginning 24 hours after MCAO, improved neuromuscular functions for nine days following the insult; and SPG stimulation for six hours per day for six days, beginning 24 hours after MCAO improved neuromuscular function at 13 and 28 days following occlusion.

Figure 6:
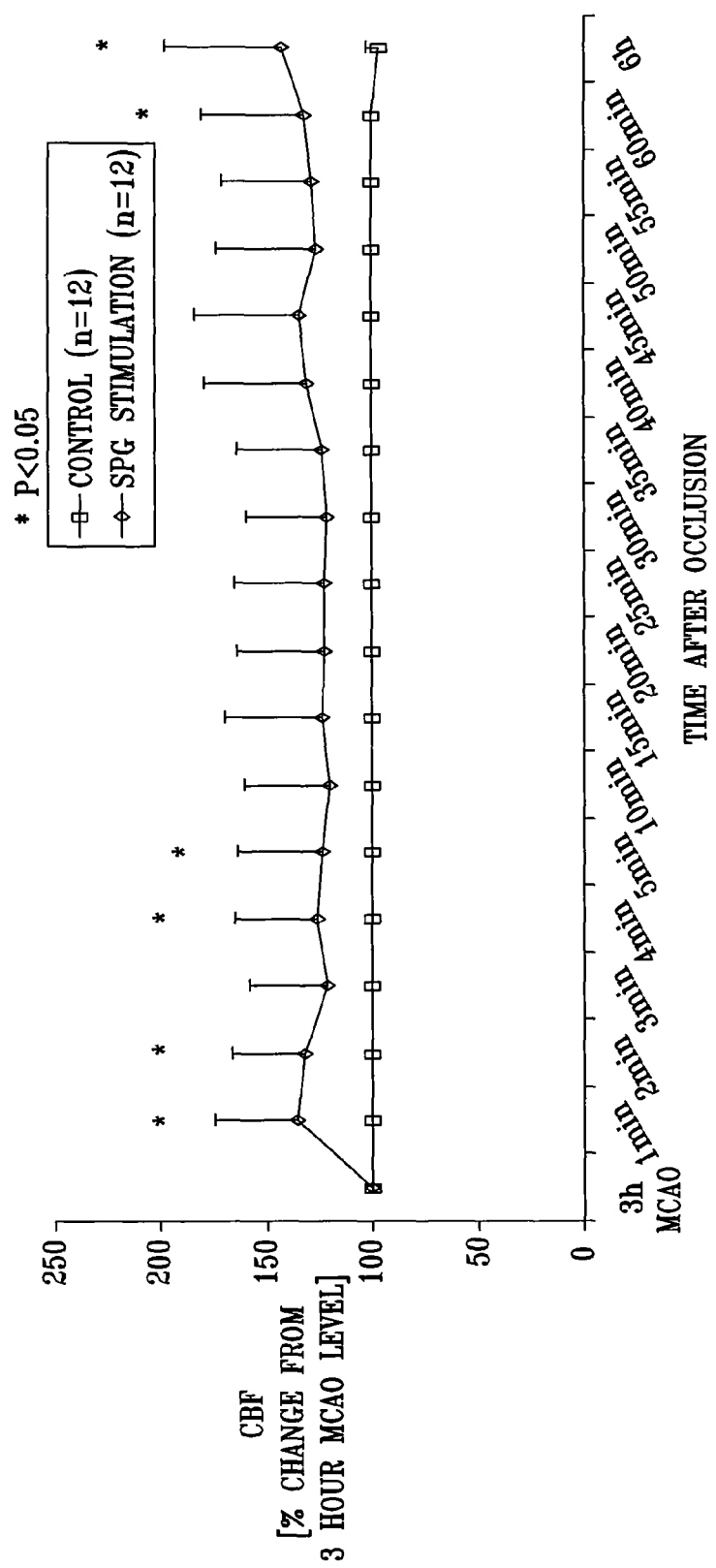
FIG. 6 is a graph showing the effect of SPG stimulation beginning three hours after permanent middle cerebral artery occlusion (pCMAO) in rats, measured in accordance with an embodiment of the present invention.

Reference is made to FIG. 6, which is a graph showing the effect of SPG stimulation beginning three hours after permanent MCAO (pCMAO) in male rats, measured in accordance with an embodiment of the present invention. The graph shows changes in CBF vs. baseline, in an experimental group (n=12) and in a control group (n=12). The Sprague Dawley® (SD) rats were anesthetized with a ketamine-xylazine combination (85 mg/kg and 5 mg/kg respectively), and pMCAO was performed as follows. The right common carotid artery (CCA) was exposed through a midline neck incision and carefully dissected free from surrounding nerves and fascia, from its bifurcation to the base of the skull. The occipital artery branches of the external carotid artery (ECA) were then isolated, and these branches were dissected and coagulated. The ECA was dissected further distally and coagulated together with the terminal lingual and maxillary artery branches, which was then divided. The internal carotid artery (ICA) was isolated and carefully separated from the adjacent vagus nerve, and the pterygopalatine artery was ligated close to its origin with a 5-0 nylon suture. A 4-0 silk suture was tied loosely around the mobilized ECA stump, and a 4 cm length of 4-0 monofilament nylon suture (the tip of the suture was blunted by using a flame, and the suture was coated with silicone, prior to insertion) was inserted through the proximal ECA into the ICA, and from there into the circle of Willis, effectively occluding the MCA. The surgical wound was closed and the rats were returned to their cages to recover from anesthesia. These techniques for performing pMCAO are similar to those described in the above-mentioned article by Schmid-Elsaesser R et al.

SPG stimulation was initiated at three hours following pMCAO. The stimulation regime included a duty cycle of 60 seconds on/12 seconds off, at 2 mA and 10 Hz, with a 500 µsec pulse width. The stimulation was applied for five minutes every 30 minutes, for a period of 10 hours. As can be seen in FIG. 6, SPG stimulation markedly and significantly increased CBF levels in rats after pMCAO. The greatest increase was observed at 6 hours following MCAO.

Figure 7:
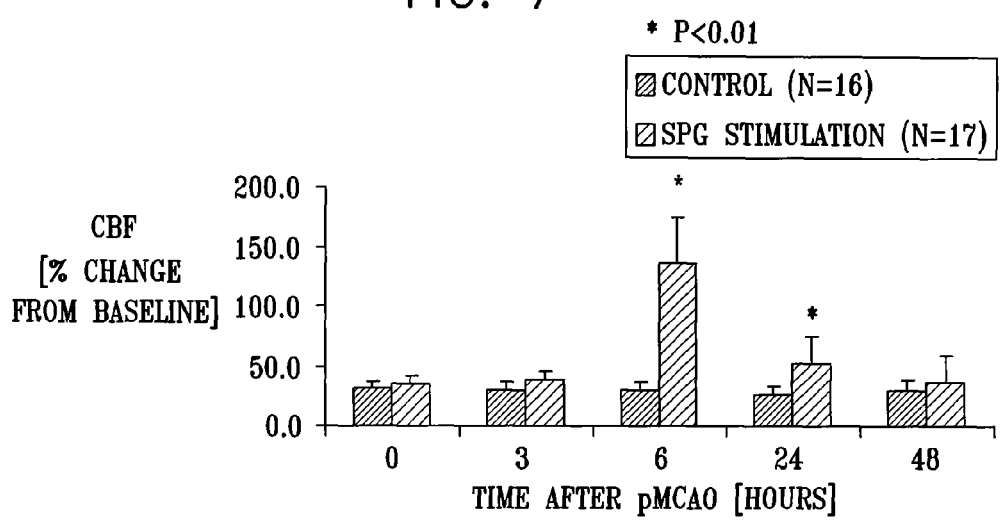
FIGS. 7 and 8 are graphs showing results of an in vivo experiment assessing the effect of SPG stimulation performed three hours following stroke, measured in accordance with an embodiment of the present invention.
Figure 8:
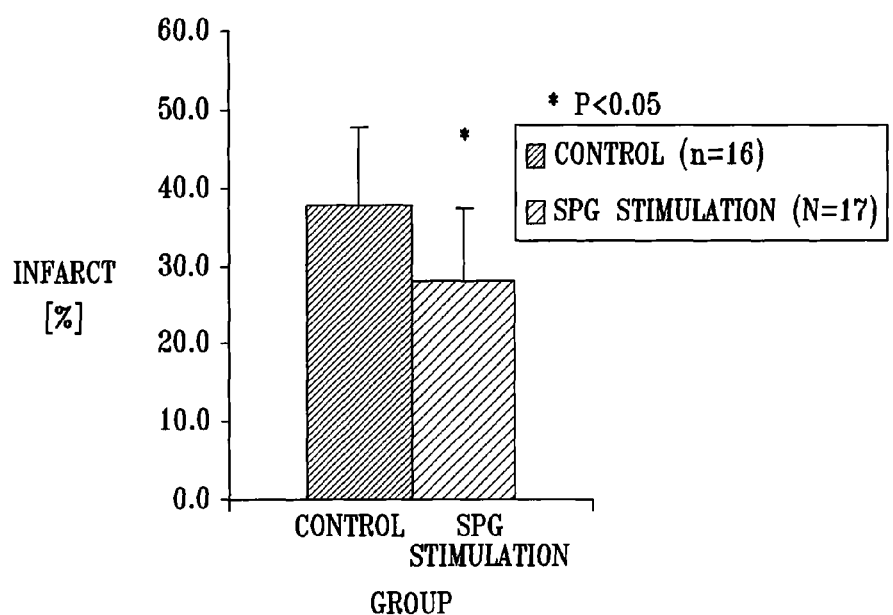

FIGS. 7 and 8 are graphs showing results of an in vivo experiment assessing the effect of SPG stimulation performed three hours following stroke, measured in accordance with an embodiment of the present invention. A rat pMCAO model of stroke was used to evaluate the neuroprotective benefits of SPG stimulation following stroke using techniques described herein. A three-hour delay prior to applying stimulation was chosen to simulate the relatively late-stage intervention common in clinical settings. The results of this experiment demonstrate that SPG stimulation provided significant neuroprotection. SPG stimulation reduced mortality, significantly improved neuromuscular function, and increased CBF.

32 SD rats were divided into an experimental group (n=15), and a control group (n=17). pMCAO was performed using the techniques described hereinabove. A bipolar electrode was brought into contact with the SPG ipsilateral to the pMCAO, and connected to a controller. Three hours after pMCAO and prior to commencement of stimulation, all of the rats were subjected to the first of three neuroscoring (behavioral) tests. Additional neuroscoring was performed at 24 and 48 hours post-pMCAO. SPG stimulation was initiated at three hours following pMCAO occlusion. The stimulation regime included a duty cycle of 60 seconds on/12 seconds off, at 2 mA and 10 Hz, with a 500 µsec pulse width. The stimulation was performed for five minutes every 30 minutes, for a period of 10 hours. Forty-eight hours following pMCAO, the rats were sacrificed, and their brains were removed for triphenyltetrazolium chloride (TTC) staining. Infarct volume was quantified at each coronal level in the area of the contralateral hemisphere and the ipsilateral spared hemisphere. The volume of the total infarct was measured. The infarct volume was quantified by computerized morphometric analysis using an imaging program.

As can be seen in FIG. 7 and in Table 3 below, SPG stimulation increased CBF levels in the experimental group vs. the control group. SPG stimulation also decreased the sub-cortical and cortical infarct volume in the experimental group vs. the control group, as measured at forty-eight hours following pMCAO, as can be seen in FIG. 8, which shows the infarct volume as a percentage of the total volume of both hemispheres, and in Table 3. Mortality was lower in the experimental group than in the control group, and neuroscore was higher in the experimental group than in the control group, as is shown in Table 3.

TABLE 3

| Group | CBF (at 6 hours after MCAO) [ml/min/100 g] | Mortality [%] | Infarct volume (at 48 hours) [%] | Neuroscore (at 24 hours) [arbitrary units] |
|---|---|---|---|---|
| Control | 99.3 | 47.1 | 38.3 | 3.3 |
| Experimental | 141.7 | 26.7 | 25.3 | 3.6 |

Figure 9A:
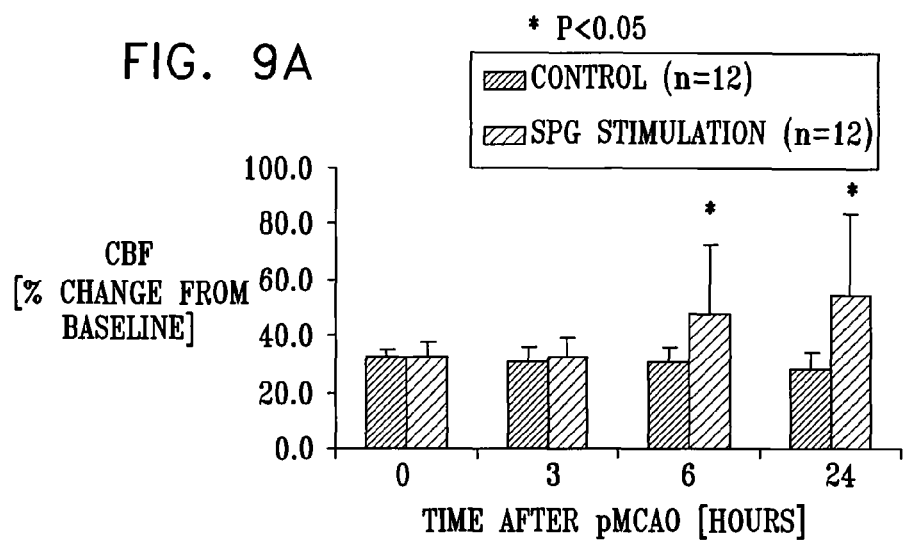
Figure 9B:
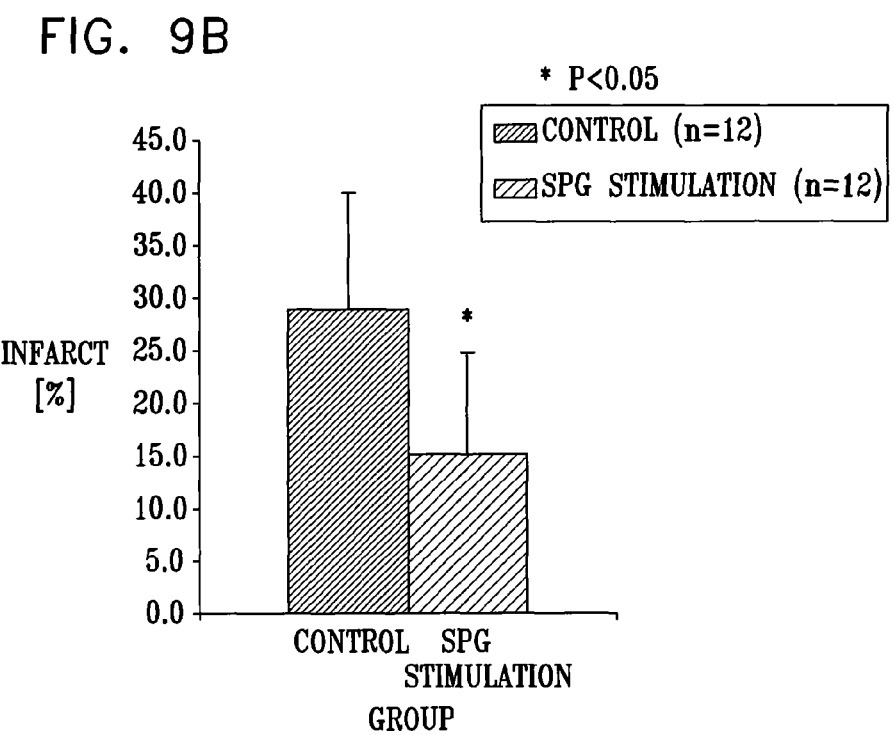

FIGS. 9A-C are graphs showing the results of in vivo experiments assessing the effect of SPG stimulation performed three hours following stroke, measured in accordance with respective embodiments of the present invention. A rat pMCAO model of stroke was used to evaluate the neuroprotective benefits of SPG stimulation following stroke using techniques described herein. Other than as described below, these experiments were conducted in the same manner as those described hereinabove with respect to FIGS. 7 and 8 and Table 3. 24 SD rats were divided into an experimental group (n=17), and a control group (n=12).

As can be seen in FIG. 9A, SPG stimulation increased CBF levels in the experimental group vs. the control group. SPG stimulation also decreased the sub-cortical and cortical infarct volume in the experimental group vs. the control group, as measured at forty-eight hours following pMCAO, as can be seen in FIG. 9B, which shows the infarct volume as a percentage of the total volume of both hemispheres. Neuroscore was slightly lower in the experimental group than in the control group at 3 hours after pMCAO, but was significantly (P<0.05) higher in the experimental group at 24 hours after pMCAO, as shown in FIG. 9C (neuroscore was assessed on a scale of 0 to 12, with 12 representing the best performance).

Reference is made to FIG. 10, which is a graph showing results of an in vivo experiment assessing the effect of rehabilitative SPG stimulation, measured in accordance with an embodiment of the present invention. A rat MCAO (middle cerebral artery occlusion) model of stroke was used to evaluate the neuromuscular benefits of rehabilitative SPG stimulation using the techniques described herein. 47 rats were divided into three groups: a control group (n=18); a first experimental group (n=16), which received one hour of SPG stimulation per day; and a second experimental group (n=13), which received three hours of SPG stimulation per day. pMCAO was performed using the techniques described hereinabove with reference to FIG. 6. A bipolar electrode was brought into contact with the SPG ipsilateral to the pMCAO, and connected to a controller. SPG stimulation was initiated at 24 hours after pMCAO, in order to demonstrate the potential rehabilitative effects of such stimulation, rather than the acute benefits. The first and second experimental groups each received SPG stimulation at 24 hours, 48 hours, and 72 hours after pMCAO. The stimulation regime included a duty cycle of 60 seconds on/12 seconds off, at 2 mA and 10 Hz, with a 500 µsec pulse width. As mentioned above, the stimulation was performed for one hour per day in the first experimental group, and three hours per day in the second experimental group.

At 24, 48, 72, 96, and 216 hours after pMCAO, the rats were tested using a modified neuroscore battery, which assessed the severity of damage on a scale of 0 to 10, with 10 representing the greatest deficit. As can be seen in FIG. 10, the rats in both the first and second experimental groups achieved better (lower) neuroscores than the control group at all tested time periods after pMCAO, with statistical significance achieved for the second (3 hour stimulation) experimental group at nine days after pMCAO.

Figure 11C:
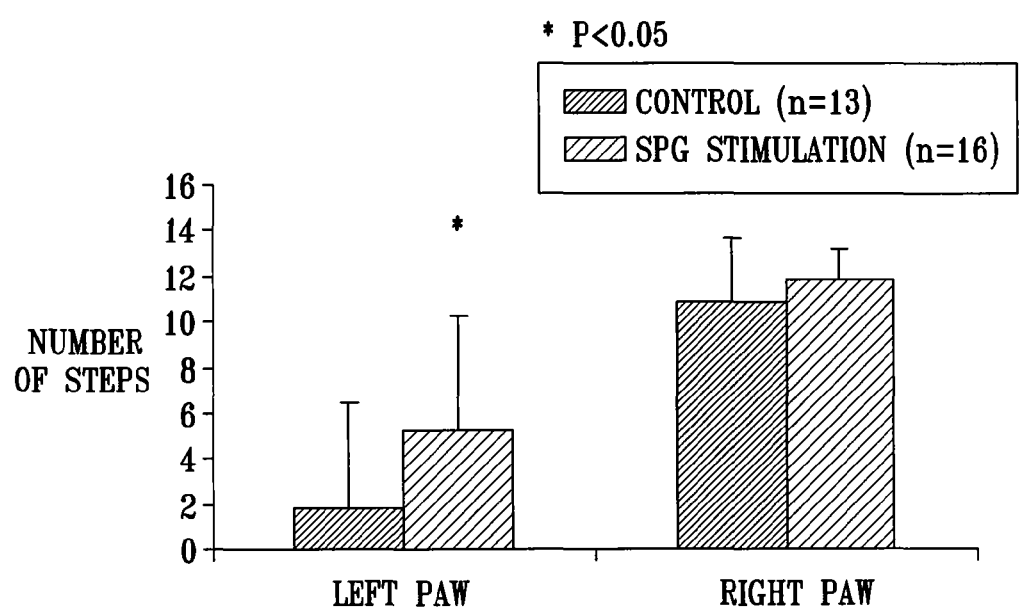

Reference is made to FIGS. 11A-C, which are graphs showing results of an in vivo experiment assessing the effect of rehabilitative SPG stimulation, measured in accordance with an embodiment of the present invention. A rat MCAO model of stroke was used to evaluate the benefits, including neuromuscular benefits, of rehabilitative SPG stimulation using the techniques described herein. 29 rats were divided into an experimental group (n=16) and a control group (n=13). Transient MCAO (tMCAO) was performed as follows. The right common carotid artery (CCA) was exposed through a midline neck incision and carefully dissected free from surrounding nerves and fascia, from its bifurcation to the base of the skull. The occipital artery branches of the external carotid artery (ECA) were isolated, and these branches were dissected and coagulated. The ECA was further dissected distally and coagulated together with the terminal lingual and maxillary artery branches, which were divided. The internal carotid artery (ICA) was isolated and carefully separated from the adjacent vagus nerve, and the pterygopalatine artery was ligated close to its origin with a 5-0 nylon suture. A 4-0 silk suture was tied loosely around the mobilized ECA stump, and a 4 cm length of 4-0 monofilament nylon suture (the tip of the suture was blunted using a flame, and the suture was coated with silicone, prior to insertion) was inserted through the proximal ECA into the ICA, and from there into the circle of Willis, effectively occluding the MCA. The suture was placed for three hours and thereafter removed. The surgical wound was closed, and the animals were returned to their cages to recover from the procedure. These techniques for performing tMCAO are similar to those described in the above-mentioned article by Schmid-Elsaesser R et al. On the day of the tMCAO procedure, a bipolar electrode was implanted in contact with the SPG ipsilateral to the tMCAO, and connected to a controller.

At 24 hours after tMCAO, and prior to commencement of the first stimulation, neurological evaluation was performed on the rats using the modified Neurological Severity Score (mNSS) scale. Only animals with an overall score of at least 12 were included in the experiment. The rats in the experimental group received SPG stimulation for 6 hours per day for 6 days, beginning 24 hours after tMCAO. The stimulation regime included a duty cycle of 60 seconds on/12 seconds off, at 2 mA and 10 Hz, with a 500 μsec pulse width. Neuroscores were assessed at days 6, 13, and 28 after tMCAO, using behavioral tests aimed at studying neuromuscular function. FIGS. 11A and 11B show results obtained at days 13 and 28, respectively (the mNSS scale ranges from 0 to 12, with best performance indicated by a 12). A significant improvement in neuromuscular function can be seen at both days 13 and 28. FIG. 11C shows the results of a stepping test for the left and right paws. A significant improvement in motor function in the experimental group compared with the control group can be seen for the contralateral (left) paw.

Reference is made to FIGS. 12A-H, which are graphs showing results of an in vivo experiment assessing the effect of long-term rehabilitative SPG stimulation, measured in accordance with an embodiment of the present invention. A rat tMCAO model of stroke was used to evaluate the benefits, including neuromuscular, motility, cognitive, somatosensory, somatomotor, infarct volume benefits, of rehabilitative SPG stimulation using the techniques described herein. The stimulation was applied for seven consecutive days beginning at 24 hours after reperfusion in the tMCAO model. 94 male Sprague Dawley (SD) rats were divided into six groups, as shown in Table 4:

TABLE 4

| Group | No. of rats | Hours of stimulation per day |
| --- | --- | --- |
| 1 - Control | 18 | N/A |
| 2 - Sham | 10 | N/A |
| 3 | 17 | 1 |
| 4 | 16 | 3 |
| 5 | 17 | 6 |
| 6 | 16 | 10 |

Prior to performance of any surgical procedure on the rats, the rats were trained using a series of behavior tests. Five parameter categories were evaluated using one or more tests, as follows:
  Neuromuscular function—rotarod motor test, mNSS test, beam walking and balance test, stepping test, and staircase skilled reaching test;
  Motility—open field test;
  Learning memory (cognitive)—water maze test;
  Somatosensory sensation—adhesive removal test; and
  Somatomotor sensation—corner turn test.

Transient MCAO (tMCAO) was performed on the right hemisphere of all of rats except those of the sham group, using the techniques described hereinabove with reference to FIGS. 11A-C. Three hours after the occlusion, reperfusion was allowed in all groups. On the day of tMCAO, the rats were anesthetized, and a bipolar electrode was implanted in contact with the SPG ipsilateral to the pMCAO (i.e., the right SPG), and connected to a controller. At 24 hours post-tMCAO Oust prior to stimulation), the rats were subjected to neuroscoring using the mNSS scale, which has a score range of 0-18, where 0 represents normal and 18 represents maximum neurological defect. Rats scoring less than or equal to 9 were excluded from the experiment.

SPG stimulation was applied for seven consecutive days beginning at 24 hours post-tMCAO, using the following regime: a duty cycle of 60 seconds on/12 seconds off, with two cycles every 15 minutes, at 2 mA and 10 Hz, with a 500 μsec pulse width. The stimulation was applied for fifteen minutes every 60 minutes. The number of hours of stimulation per day was as shown in Table 4 above.

In order to assess rehabilitation, on days 8, 14, and 35 post-tMCAO, (with limited exceptions for specific tests), the rats were subjected to the same pre-procedure behavior tests used in the training, as described hereinabove. One day after the last behavior testing, the rats were sacrificed and perfused. Their brains were harvested, infarct volume was measured, and neurons were counted.

The results of the experiment included the following:
  Mortality in the SPG-stimulated groups was lower than in the non-stimulated control group.
  SPG stimulation generally improved neuromuscular functions (rotarod, mNSS, beam walk and balance, stepping and staircase tests) in comparison to the non-stimulated control group.
  SPG stimulation improved cognitive capabilities (water maze test) in comparison to the non-stimulated control group.
  There was a trend towards increased motility (open field test) in the SPG-stimulated groups.
  Somatosensory sensations were enhanced in the SPG-stimulated groups in comparison to the non-stimulated control group.

Somatomotor competence was superior in the SPG-stimulated groups than in the non-stimulated control groups.

SPG stimulation resulted in higher neurons counts in cortical layer V of the ipsilateral stimulated side in comparison to the non-stimulated control group.

In summary, in the present experiment, SPG stimulation initiated 24 hours after tMCAO had advantageous results for all five parameter groups evaluated. In addition, SPG stimulation increased the number of neurons in all regions counted.

FIG. 12A is a graph showing neuroscores (mNSS test) of all six groups, measured at 24 hours, 8 days, 14 days, and 35 days after tMCAO, measured in accordance with an embodiment of the present invention. As can be seen in the graph, mNSS scores of the SPG-stimulated rats decreased in a time-dependent manner post-tMCAO, indicating the occurrence of an active restorative, rehabilitative process. SPG stimulation markedly and significantly ($p<0.05$) improved neurological function measured at days 8, 14, and 35 in all SPG-stimulated groups.

FIG. 12B is a graph showing the results of the stepping test performed on the left foreleg in all six groups, measured pre-tMCAO and at 8 days, 14 days, and 35 days after tMCAO, measured in accordance with an embodiment of the present invention. As can be seen in the graph, there was a significant ($p<0.05$) increase in left (impaired) foreleg stepping in all SPG-stimulated rats in comparison to the non-stimulated control group (with the exception of the 10-hour stimulated group at day 35). Maximum improvement was evident in the 3- and 6-hour stimulation groups at days 14 and 35, respectively.

FIGS. 12C-F are graphs showing the results of the Morris water maze (WM) task, measured in accordance with an embodiment of the present invention. The Morris WM task is a standard test of learning in which the animal repeatedly searches for a rest platform hidden beneath the surface in a pool. The test is especially sensitive to hippocampal and cortical damage, and reflects attention, memory, and learning strategy. The Morris WM task was performed on days 14 and 35 following tMCAO.

Figure 12C:
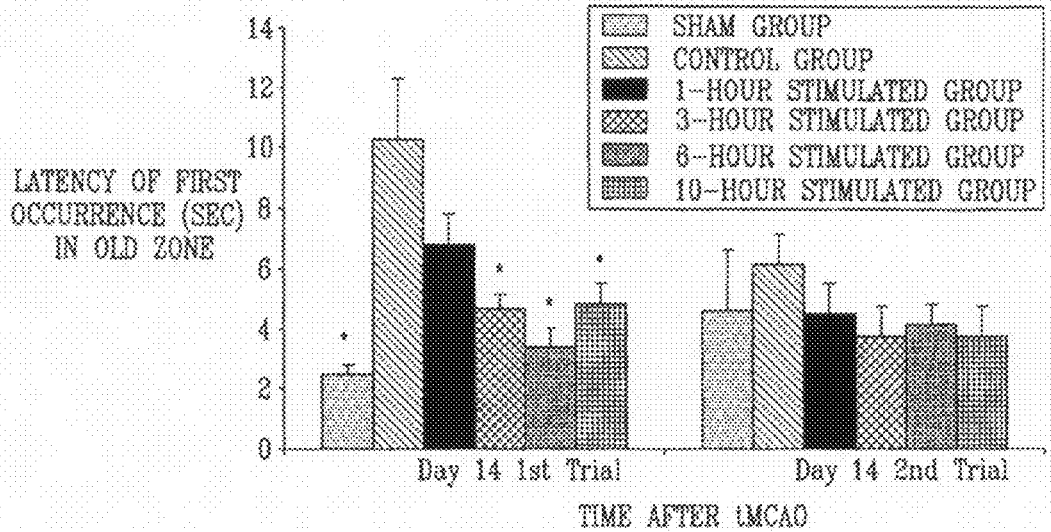

FIG. 12C is a graph showing the latency to the first occurrence in the Old Zone (as described below) in first and second trials at 14 days after tMCAO, measured in accordance with an embodiment of the present invention. This parameter assesses the rats' functional memory. The rest platform was moved from the Old Zone (its position during training) to the New Zone (its position during testing), and the rats were expected to seek the Old Zone. The first trial showed that the SPG-stimulated rats (3-, 6-, and 10-hour stimulation) returned to the Old Zone significantly ($p<0.05$) more quickly than the non-stimulated rats in the control group. The second trial showed, although non-significantly, that the SPG-stimulated rats returned to the Old Zone faster than the non-stimulated controls, even though introduced to the New Zone rest platform in the first trial. The second trial thus confirmed that the SPG-stimulated rats showed enhanced remnants of functional memory.

Figure 12D:
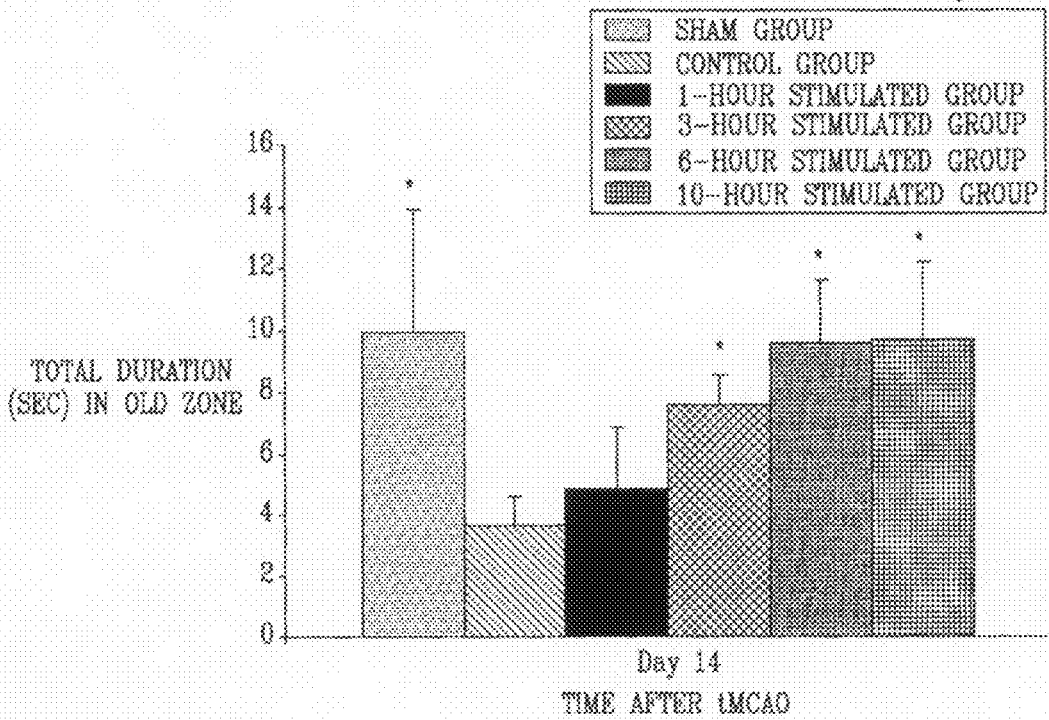

FIG. 12D is a graph showing time spent in the Old Zone at day 14 after tMCAO, measured in accordance with an embodiment of the present invention. This parameter also assesses the rats' functional memory. As can be seen in the graph, the 3-, 6-, and 10-hour SPG-stimulated groups spent significantly ($p<0.05$) more time seeking the rest platform in the Old Zone in comparison to the non-stimulated control group.

FIG. 12E is a graph showing the latency to the first occurrence in the New Zone in first and second trials at day 35 after tMCAO, measured in accordance with an embodiment of the present invention. This parameter also assessed the rats' functional memory. In the first trial, the 3-, 6-, and 10-hour SPG-stimulated groups demonstrated superior, although non-significant, results in finding the New Zone, compared with the non-stimulated control group. In the second trial, all of the SPG-stimulated groups achieved better results than the non-stimulated control group. These results were significant ($p<0.05$) only in the 3-hour stimulated group.

FIG. 12F is a graph showing the distance moved to find the rest platform in the New Zone in first and second trials at day 35 after tMCAO, measured in accordance with an embodiment of the present invention. This parameter assessed the rats' long-term learning capability. In both trials the SPG-stimulated rats demonstrated better performance than the control group. These results were significant ($p<0.05$) only in the 3-hour stimulated group during the first trial.

The staircase test (results not shown) was performed to assess the rehabilitation of foreleg fine motorics. At day 14 after tMCAO the SPG-stimulated groups demonstrated better performance in the left impaired foreleg than the control group (1-, 3-, and 6-hour stimulation, significant ($p<0.05$) in the 3- and 6-hour stimulated rats only). At day 35 after tMCAO the SPG-stimulated groups demonstrated better performance in the left impaired foreleg, significant ($p<0.05$) in the 3-hour stimulated rats only.

The rotarod test (results not shown) was performed to assess the rats' ability to remain on a rotating rod. It requires a high degree of sensorimotor coordination and is sensitive to damage in the basal ganglia and the cerebellum. The only significant ($p<0.05$) results were in the 3-hour stimulated rats on the 35 day assessment, which remained on the rotarod significantly longer than the control group.

FIG. 12G is a graph showing the time required for the rats to remove an adhesive patch from the left foreleg, measured in accordance with an embodiment of the present invention. This test assessed both cutaneous sensitivity and sensor motor integration, and is analogous to human neurological tests used clinically in stroke patients. In the left impaired foreleg, the SPG-stimulated rats showed better results than the non-stimulated controls at all assessment days (8, 14, and 35 days). These results were significant ($p<0.05$) at all three assessment days in the 3- and 6-hour stimulated groups only.

The corner test (results not shown) was performed to evaluate the rats' tendency to favor a turn in the direction of the ipsilateral side of the tMCAO (i.e., the right side in the experiment). On all three assessment days (8, 14, and 35 days), all SPG-stimulated groups showed a decrease in right side turns in comparison to the non-stimulated control group. This decrease was significant ($p<0.05$) only on day 35 in the 1- and 6-hour stimulated rats.

The beam walk test (results not shown) was performed to evaluate sensor motor integration, specifically hind limb function. In general, all SPG-stimulated groups showed improved results in comparison to the non-stimulated control group. These results were significant ($p<0.05$) only on day 35 only in the 3-hour stimulated group.

The beam balance test (results not shown) was performed to assess gross vestibulomotor function, by requiring the rats to balance steadily on a narrow beam. This test is sensitive to motor cortical insults. On all assessment days (days 8, 14, and 35), all of the SPG-stimulated groups (except the 1-hour stimulated group on day 8) performed better than the non-stimulated control group. These results were significant ($p<0.05$) only on day 14 in the 3-hour stimulated group.

The open field test (results not shown) was performed to assess the following four parameters indicative of hippocampal and basal ganglia damage, as well as hind limb dysfunction:

Total distance moved, which decreases in cerebrally-insulted animals. All of the SPG-stimulated groups achieved enhanced movement compared to the control group on day 14 after tMCAO. These results were significant ($p<0.05$) only in the 3- and 6-hour stimulated groups.

Velocity, which is diminished in cerebrally-insulted animals. All of the SPG-stimulated groups achieved enhanced velocity compared to the control group on day 14 after tMCAO. These results were significant ($p<0.05$) only in the 3- and 6-hour stimulated groups.

Latency of first occurrence in center zone. All of SPG-stimulated groups (except the 10-hour stimulated group on day 14) showed quicker entry into the center zone in comparison to the non-stimulated control group. These results were significant ($p<0.05$) only on day 35 in the 1- and 3-hour stimulated groups.

Total distance moved in center zone. On day 14, the 3- and 10-hour stimulated groups achieved significantly ($p<0.05$) greater distance moved than the control group.

FIG. 12H is a graph showing the number of neurons in cortical layer V and II-III, measured in accordance with an embodiment of the present invention. Neuron counting was performed in cortical layers V and II-III in the non-stimulated control group and in the 3- and 6-hour SPG-stimulated groups. The number of neurons in cortical layer V was significantly ($p<0.05$) greater in both of these SPG-stimulated groups compared to the non-stimulated group. In cortical layers II-III there was no significant difference between the stimulated and non-stimulated groups.

There were no significant differences in body weigh between the SPG-stimulated groups and the non-stimulated control group.

The inventors are currently performing an in vivo experiment to compare the application of SPG stimulation for 28 days with the application of SPG stimulation for 7 days, as applied in the experiment described hereinabove with reference to FIGS. 12A-H. The experimental protocol is similar to that of this above-mentioned experiment. Preliminary results of this current experiment indicate that application of SPG stimulation for the longer 28-day period has greater therapeutic benefits than application of the stimulation for 7 days.

Table 5 shows the results of an in vivo experiment performed to test whether long-term stimulation of the SPG using a protocol appropriate for treating stroke damages the BBB, measured in accordance with an embodiment of the present invention. 31 rats (males, Wistar™, 12 weeks, average body weight 300 g) were divided to three groups: an SPG stimulation group (n=13), which had an SPG stimulator implanted; a first control group (n–12), which was not stimulated, and had a sham operation; and a second control group (n=6), which had a sham operation, and was exposed to an RF electromagnetic field for 24 hours. The SPG stimulation group received 24 hours of continuous SPG stimulation with a stimulation regime that included a duty cycle of 90 seconds on/60 seconds off, at 5 V and 10 Hz, with a 1 millisecond pulse width. Upon completion of stimulation, a marker (Evans blue (EB) (2%)), which normally does not cross the BBB, was intravenously (2 ml) injected into the rats. 48 hours following the EB administration, 500 ml of cold saline was used for perfusion of blood and EB from the rats' circulation. Thereafter, the rats' brains were removed, the left and right hemispheres were homogenized, and brain EB concentration was determined using an Elisa Reader at 630 nm. As can be seen in Table 5, stimulation for 24 hours did not cause leakage of EB into the brain, indicating that the stimulation did not cause damage to the BBB.

TABLE 5

| Group | Right Hemisphere | Left Hemisphere |
|---|---|---|
| First Control (non-stimulated) (n = 12) | 0.04 ± 0.03 | 0.02 ± 0.02 |
| Second Control (RF-exposed) (n = 6) | 0.03 ± 0.02 | 0.04 ± 0.02 |
| Experimental (stimulated) (n = 13) | 0.03 ± 0.02 | 0.02 ± 0.02 |

The inventors performed in vivo experiments in rats to assess the safety of SPG stimulation techniques described herein. These experiments showed that stimulation did not break down the BBB, and that stimulation was found to be safe in a battery of motor and cognitive tests, which were in general agreement with histological analysis.

In an embodiment of the present invention, a calibration procedure is performed, in which a test molecule is injected into the systemic blood circulation of the subject, and a threshold stimulation strength is determined by stimulating at least one MTS, and gradually increasing the stimulation strength until the BBB is opened (e.g., as determined using a radioactive scanning technique). System 10 applies therapeutic stimulation to an MTS using a strength equal to a certain percentage of the threshold strength, typically less than 100%.

Reference is made to FIG. 13, which is a graph 160 showing a protocol for treating a brain tumor, in accordance with an embodiment of the present invention. In accordance with this protocol, a method for treating a brain tumor comprises: (a) during a first period of time 170, applying excitatory electrical stimulation to at least one MTS at a first, relatively low strength 152, in conjunction with administration of a chemotherapeutic drug at a first, relatively high dosage 174; and (b) during a second period of time 176, applying the stimulation at a second strength 178 greater than first strength 152, in conjunction with administration of the drug at a second dosage 180 lower than first dosage 174. Alternatively, the drug is administered only at the first dosage, and the stimulation is applied at second strength 178 after the level of the drug in the systemic circulation has dropped because of ordinary metabolic drug clearance from the circulation. For some applications, the protocol shown for second period 176 is applied after first period 170 (as shown). For other applications, the protocol shown for the second period is applied before the protocol shown for the first period. Alternatively, two different chemotherapeutic drugs are applied during the first and second periods, respectively, not necessarily at different dosages.

The blood-tumor barrier (BTB) of the core and tissue near the core of a growing brain tumor is generally damaged by the natural progression of the tumor. During first period 170, stimulation applied at first strength 172 is thus sufficient to further open the BTB of the core and tissue near the core, but not sufficient to open the BBB of the periphery of the tumor or of other cells in the brain. In other words, first strength 172 is between a BTB opening strength 173 and maximum BBB-opening strength 112. As a result, high dosage 174 of the chemotherapeutic drug is targeted at the core and tissue near the core of the tumor, since the drug is substantially unable to enter other brain cells, because of their intact BBB and the large molecular size of the drug. During second period 176, stimulation at higher second strength 178 opens the BBB of other brain cells, including tumor cells in the periphery of the core and/or other areas of the brain. For some applications, second strength 178 is greater than or equal to maximum BBB-opening strength 112, as shown in FIG. 13. Alternatively or additionally, second strength 178 is sufficient to induce a significant increase in the permeability of the BBB. Second dosage 180 is low enough not to substantially damage non-tumor cells. For some applications, the dosage is set to the highest level that does not cause systemic and/or brain toxicity; this level is higher during first period 170 than during second period 176, because of the lower level of MTS stimulation during the first period than during the second period. For some applications, only the protocol for the first period is applied, when this is deemed sufficient to facilitate delivery of the drug to the core and tissue near the core while generally avoiding facilitating delivery of the drug into other brain cells. For some applications, in order to determine the appropriate parameters for increasing the permeability of the BTB and/or BBB for this embodiment, a calibration procedure is performed in which the uptake of a substance across the BTB and/or BBB is measured at a plurality of stimulation parameters (e.g., using a radioactive isotope or other marker known in the art).

In an embodiment of the present invention, bipolar stimulation is applied, in which a first electrode is applied to a first MTS, and a second electrode is applied to a second MTS.

In an embodiment of the present invention, an SPG of the subject is indirectly activated by stimulating a branch of cranial nerve V of the subject, including, for example, afferent fibers of cranial nerve V, either electrically, magnetically, or electromagnetically. A reflex response to such stimulation leads to activation of the SPG. Typically, the stimulation is performed while the subject is under general anesthesia or sedation. For some applications, cranial nerve V is stimulated by non-invasively attaching electrodes to the surface of the face of the subject, typically using techniques commonly used for transcutaneous electrical nerve stimulation (TENS).

In an embodiment of the present invention, an SPG of the subject is indirectly activated by stimulating afferent fibers of the trigeminal nerve (cranial nerve V) of the subject, either electrically, magnetically, or electromagnetically. A reflex response to such stimulation leads to activation of the SPG. (For example, the maxillary branch of the trigeminal nerve directly contacts the SPG.) Typically, but not necessarily, such stimulation is performed while the subject is under general anesthesia or sedation. For some applications, cranial nerve V is stimulated by non-invasively attaching electrodes to the surface of the face of the subject, typically using techniques commonly used for transcutaneous electrical nerve stimulation (TENS). For example, TENS may be applied to a cheek or a tip of a nose of a subject. In an embodiment of the present invention, an oral appliance is provided that is configured to be brought into contact with a mucous membrane of a palate of an oral cavity of a subject. The appliance comprises one or more electrodes, which are driven to apply transmucosal electrical stimulation to nerve fibers within or immediately above the mucous membrane, which fibers directly innervate an SPG of the subject. Typically, but not necessarily, such stimulation is performed while the subject is under general anesthesia or sedation. Such transmucosal stimulation may require less current than the transcutaneous stimulation described hereinabove.

In some embodiments of the present invention, techniques described herein are practiced in combination with techniques described in one or more of the references cited in the Background of the Invention section hereinabove and/or in combination with techniques described in one or more of the patent applications cited hereinabove.

The scope of the present invention includes embodiments described in the following patent applications, which are assigned to the assignee of the present patent application and are incorporated herein by reference. In an embodiment of the present invention, techniques and apparatus described in one or more of the following applications are combined with techniques and apparatus described herein:

U.S. Provisional Patent Application 60/203,172, filed May 8, 2000, entitled, "Method and apparatus for stimulating the sphenopalatine ganglion to modify properties of the BBB and cerebral blood flow"

U.S. patent application Ser. No. 10/258,714, filed Oct. 25, 2002, entitled, "Method and apparatus for stimulating the sphenopalatine ganglion to modify properties of the BBB and cerebral blood flow," or the above-referenced PCT Publication WO 01/85094

U.S. Provisional Patent Application 60/364,451, filed Mar. 15, 2002, entitled, "Applications of stimulating the sphenopalatine ganglion (SPG)"

U.S. Provisional Patent Application 60/368,657, filed Mar. 28, 2002, entitled, "SPG Stimulation"

U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head"

U.S. Provisional Patent Application 60/388,931, filed Jun. 14, 2002, entitled "Methods and systems for management of Alzheimer's disease," PCT Patent Application PCT/IL03/000508, filed Jun. 13, 2003, claiming priority therefrom, and a U.S. patent application filed Dec. 14, 2004 in the national stage thereof U.S. Provisional Patent Application 60/400,167, filed Jul. 31, 2002, entitled, "Delivering compounds to the brain by modifying properties of the BBB and cerebral circulation"

U.S. Provisional Patent Application 60/426,180, filed Nov. 14, 2002, entitled, "Surgical tools and techniques for sphenopalatine ganglion stimulation," PCT Patent Application PCT/IL03/000966, filed Nov. 13, 2003, which claims priority therefrom, and a U.S. patent application filed May 11, 2005 in the national stage thereof U.S. Provisional Patent Application 60/426,182, filed Nov. 14, 2002, and corresponding PCT Patent Application PCT/IL03/000967, which claims priority therefrom, filed Nov. 13, 2003, entitled, "Stimulation circuitry and control of electronic medical device," and a U.S. patent application filed May 11, 2005 in the national stage thereof U.S. patent application Ser. No. 10/294,310, filed Nov. 14, 2002, entitled, "SPG stimulation for treating eye pathologies," which published as U.S. Patent Application Publication 2003/0176898, and PCT Patent Application PCT/IL03/000965, filed Nov. 13, 2003, claiming priority therefrom PCT Patent Application PCT/IL03/000631, filed Jul. 31, 2003, entitled, "Delivering compounds to the brain by modifying properties of the BBB and cerebral circulation," which published as PCT Publication WO 04/010923, and U.S. patent application Ser. No. 10/522,615 in the national stage thereof U.S. Pat. No. 6,853,858 to Shalev U.S. patent application Ser. No. 10/783,113, filed Feb. 20, 2004, entitled, "Stimulation for acute conditions," which published as US Patent Application Publication 2004/0220644

U.S. Provisional Patent Application 60/426,181, filed Nov. 14, 2002, entitled, "Stimulation for treating ear pathologies," PCT Patent Application PCT/IL03/000963, filed Nov. 13, 2003, which claims priority therefrom, and which published as PCT Publication WO 04/045242, and U.S. patent application Ser. No. 10/535,025 in the national stage thereof U.S. Provisional Patent Application 60/448,807, filed Feb. 20, 2003, entitled, "Stimulation for treating autoimmune-related disorders of the CNS"

U.S. Provisional Patent Application 60/461,232 to Gross et al., filed Apr. 8, 2003, entitled, "Treating abnormal conditions of the mind and body by modifying properties of the blood-brain barrier and cephalic blood flow"

PCT Patent Application PCT/IL03/00338 to Shalev, filed Apr. 25, 2003, entitled, "Methods and apparatus for modifying properties of the BBB and cerebral circulation by using the neuroexcitatory and/or neuroinhibitory effects of odorants on nerves in the head," and U.S. patent application Ser. No. 10/512,780, filed Oct. 25, 2004 in the national stage thereof, which published as US Patent Application 2005/0266099

U.S. Provisional Patent Application 60/506,165, filed Sep. 26, 2003, entitled, "Diagnostic applications of stimulation"

U.S. patent application Ser. No. 10/678,730, filed Oct. 2, 2003, entitled, "Targeted release of nitric oxide in the brain circulation for opening the BBB," which published as US Patent Application 2005/0074506, and PCT Patent Application PCT/IL04/000911, filed Oct. 3, 2004, claiming priority therefrom PCT Patent Application PCT/IL04/000897, filed Sep. 26, 2004, entitled, "Stimulation for treating and diagnosing conditions," which published as PCT Publication WO 05/030025

U.S. Provisional Patent Application 60/604,037, filed Aug. 23, 2004, entitled, "Concurrent bilateral SPG modulation"

PCT Patent Application PCT/IL05/000912, filed Aug. 23, 2005, entitled, "Concurrent bilateral SPG modulation," which published as PCT Publication WO 06/021957

U.S. patent application Ser. No. 10/952,536, filed Sep. 27, 2004, entitled, "Stimulation for treating and diagnosing conditions," which published as US Patent Application Publication 2005/0159790

U.S. patent application Ser. No. 11/349,020, filed Feb. 7, 2006, entitled, "SPG stimulation via the greater palatine canal"

In an embodiment of the present invention, electrical stimulation system 10 comprises circuitry described in one or more of the above-mentioned applications.

In an embodiment of the present invention, an MTS is stimulated using the magnetic stimulation apparatus and methods described in the above-mentioned U.S. patent application Ser. No. 10/783,113.

As used in the present application and in the claims, the BBB comprises the tight junctions opposing the passage of most ions and large molecular weight compounds between the blood and brain tissue. As used in the present application and in the claims, the BTB comprises a barrier opposing the passage of many ions and large molecular weight compounds between the blood and tissue of a brain tumor.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may, alternatively, be coupled in a wired fashion, and apparatus for communication and power transmission which are shown to be coupled in a wired fashion may, alternatively, be coupled in a wireless fashion.

The invention claimed is:

1. A method for treatment, comprising:
   identifying that a subject suffers from an adverse cerebrovascular condition, excluding Alzheimer's disease and Parkinson's disease;
   responsively to the identifying, applying electrical stimulation to a site of the subject during a plurality of stimulation periods which includes at least first and last stimulation periods, the site selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve;
   setting an inter-period interval between initiation of the first stimulation period and initiation of the last stimulation period to be at least 24 hours; and
   configuring the stimulation during the first and last stimulation periods to induce at least one neuroprotective occurrence selected from the group consisting of: an increase in cerebral blood flow (CBF) of the subject, and a release of one or more neuroprotective substances.

2. The method according to claim 1, wherein setting the inter-period interval comprises setting the inter-period interval to be no more than a maximum value.

3. The method according to claim 1, wherein setting the inter-period interval comprises setting the inter-period interval to be no more than nine months.

4. The method according to claim 1, wherein applying the stimulation comprises storing a maximum total time of stimulation per each time period having a given duration, and applying the stimulation no more than the maximum total time per each time period having the given duration.

5. The method according to claim 1, wherein the plurality of stimulation periods includes at least one second stimulation period between the first and last stimulation periods, wherein applying the stimulation comprises applying the stimulation during the first, second, and last stimulation periods, and wherein configuring the stimulation comprises configuring the stimulation during the first, second, and last stimulation periods to induce the at least one neuroprotective occurrence.

6. The method according to claim 1, wherein the initiation of the last stimulation period occurs simultaneously with a conclusion of the first stimulation period, and wherein applying the stimulation during the first and last stimulation periods comprises applying the stimulation continuously from the initiation of the first stimulation period to a conclusion of the last stimulation period.

7. The method according to claim 1, wherein the initiation of the last stimulation period occurs after a conclusion of the first stimulation period, and wherein applying the stimulation during the first and last stimulation periods comprises withholding applying the stimulation during at least one non-stimulation period between the conclusion of the first stimulation period and the initiation of the last stimulation period.

8. The method according to claim 1, wherein the adverse cerebrovascular condition includes an ischemic stroke, and wherein identifying that the subject suffers from the condition comprises identifying that the subject has experienced the ischemic stroke.

9. The method according to claim 1, wherein configuring the stimulation comprises setting a strength of the stimulation during at least one of the plurality of stimulation periods to be less than 40% of a strength that induces a maximum increase in CBF in the subject that is achievable by applying the stimulation.

10. The method according to claim 1, wherein configuring the stimulation comprises setting a strength of the stimulation during at least one of the plurality of stimulation periods to a level that induces less than 40% of a maximum increase in CBF in the subject that is achievable by applying the stimulation.

11. The method according to claim 1, wherein applying the stimulation during the first and last stimulation periods comprises applying the stimulation for less than six hours during each of the first and last stimulation periods.

12. The method according to claim 1, wherein applying the stimulation during the first and last stimulation periods comprises applying the stimulation for between one and six hours during each of the first and last stimulation periods.

13. The method according to claim 1, wherein applying the stimulation comprises placing an electrical stimulator in a vicinity of the site, and activating the stimulator to apply the stimulation.

14. The method according to claim 1, wherein setting the inter-period interval comprises setting the inter-period interval to be at least 48 hours.

15. The method according to claim 14, wherein setting the inter-period interval comprises setting the inter-period interval to be at least one week.

16. The method according to claim 15, wherein the plurality of stimulation periods includes a plurality of daily stimulation periods, wherein applying the stimulation comprises applying the stimulation during at least one of the daily stimulation periods on every day between the initiation of the first stimulation period and the initiation of the last stimulation period, and wherein configuring the stimulation comprises configuring the stimulation during the plurality of daily stimulation periods to induce the at least one neuroprotective occurrence.

17. The method according to claim 16, wherein applying the stimulation comprises applying the stimulation for at least 30 minutes every day between the initiation of the first stimulation period and the initiation of the last stimulation period.

18. The method according to claim 17, wherein applying the stimulation comprises applying the stimulation for at least 60 minutes every day between the initiation of the first stimulation period and the initiation of the last stimulation period.

19. The method according to claim 15, wherein setting the inter-period interval comprises setting the inter-period interval to be at least two weeks.

20. The method according to claim 19, wherein setting the inter-period interval comprises setting the inter-period interval to be at least four weeks.

21. The method according to claim 1, wherein the condition includes an adverse cerebrovascular event, wherein identifying that the subject suffers from the condition comprises identifying that the subject has experienced the event, and wherein applying the stimulation comprises applying the stimulation beginning at least three hours after the event.

22. The method according to claim 21, wherein applying the stimulation comprises applying the stimulation beginning at least six hours after the event.

23. The method according to claim 22, wherein applying the stimulation comprises applying the stimulation beginning at least nine hours after the event.

24. The method according to claim 23, wherein applying the stimulation comprises applying the stimulation beginning at least 12 hours after the event.

25. The method according to claim 24, wherein applying the stimulation comprises applying the stimulation beginning at least 24 hours after the event.

26. The method according to claim 1, wherein configuring the stimulation comprises setting a strength of the stimulation during at least one of the plurality of stimulation periods to be insufficient to induce a significant increase in permeability of a blood-brain barrier (BBB) of the subject.

27. The method according to claim 26, wherein setting the strength comprises setting the strength of the stimulation during the at least one of the plurality of stimulation periods to be less than 40% of a strength that is sufficient to induce the significant increase in permeability of the BBB.

28. The method according to claim 1, wherein the site includes the SPG, and wherein applying the stimulation comprises applying the stimulation to the SPG.

29. The method according to claim 28, wherein applying the stimulation comprises:
placing an elongated support element within a greater palatine canal of the subject, sized to extend from a palate of the subject to the SPG, and having a distal end; and
applying the stimulation from a vicinity of the distal end of the support element.

30. The method according to claim 1, wherein applying the stimulation comprises applying the stimulation during the first period at a first stimulation strength and during the last period at a second stimulation strength, and setting the second stimulation strength to be different from the first stimulation strength.

31. The method according to claim 30, wherein setting the second stimulation strength comprises setting the second stimulation strength to be less than the first stimulation strength.

32. The method according to claim 1, wherein an interval between a conclusion of the first stimulation period and the initiation of the last stimulation period is zero.

* * * * *